US012775000B1

(12) United States Patent
Christodouleas et al.

(10) Patent No.: US 12,775,000 B1
(45) Date of Patent: Oct. 27, 2026

(54) METHODS AND DEVICES FOR BACTERIA DETECTION USING FLOW PERMEABLE SENSORS

(71) Applicant: University of Massachusetts, Boston, MA (US)

(72) Inventors: Dionysios Christodouleas, Winchester, MA (US); Parthena Chorti, Raleigh, NC (US); Abbas Parvez Kazi, Lowell, MA (US); Al Monsur Jiaul Haque, Lowell, MA (US)

(73) Assignee: University of Massachusetts, Westborough, MA (US)

( * ) Notice: Subject to any disclaimer, the term of this patent is extended or adjusted under 35 U.S.C. 154(b) by 1212 days.

(21) Appl. No.: 17/656,320

(22) Filed: Mar. 24, 2022

Related U.S. Application Data

(60) Provisional application No. 63/165,334, filed on Mar. 24, 2021.

(51) Int. Cl.
*G01N 1/00* (2006.01)
*C07K 16/12* (2006.01)
*C12Q 1/28* (2006.01)
*C12Q 1/689* (2018.01)
*G01N 33/14* (2006.01)
*G01N 33/18* (2006.01)

(52) U.S. Cl.
CPC ............ *G01N 33/14* (2013.01); *C07K 16/12* (2013.01); *C12Q 1/28* (2013.01); *C12Q 1/689* (2013.01); *G01N 33/18* (2013.01)

(58) Field of Classification Search
None
See application file for complete search history.

(56) References Cited

U.S. PATENT DOCUMENTS 11,291,997 B2 * 4/2022 Henry ............... B01L 3/502746

* cited by examiner

*Primary Examiner* — Jyoti Mutreja
(74) *Attorney, Agent, or Firm* — Joshua A. Stockwell, Esq.

(57) ABSTRACT

Devices and methods for the detection of bacteria in liquid samples (e.g., water, beverages, juices etc.) or bacteria in liquid media derived from solid samples incubated in broth media are disclosed. The devices and methods may be used to analyze any volume of sample (from few microliters to hundred milliliters) and may detect a single bacterium in the tested volume of the sample.

21 Claims, 42 Drawing Sheets

| aliquot volume (mL) | number of bacteria in 100 mL | | | | | | | | |
|---|---|---|---|---|---|---|---|---|---|
| | 1 | 3 | 5 | 10 | 20 | 50 | 100 | 500 | 1000 |
| 0.1 | 0.3 | 1 | 2 | 3 | 6 | 14 | 26 | 77 | 95 |
| 0.3 | 1 | 3 | 4 | 7 | 16 | 36 | 60 | 99 | 100 |
| 1 | 3 | 9 | 14 | 26 | 45 | 78 | 95 | 100 | 100 |
| 5 | 15 | 38 | 55 | 80 | 96 | 100 | 100 | 100 | 100 |
| 10 | 30 | 65 | 83 | 97 | 100 | 100 | 100 | 100 | 100 |

| aliquot volume (mL) | number of bacteria in 100 mL | | | | | | | | |
|---|---|---|---|---|---|---|---|---|---|
| | 1 | 3 | 5 | 10 | 20 | 50 | 100 | 500 | 1000 |
| 0.1 | 0.3 | 1 | 2 | 3 | 6 | 14 | 25 | 77 | 95 |
| 0.3 | 1 | 3 | 4 | 7 | 16 | 36 | 60 | 99 | 100 |
| 1 | 3 | 9 | 14 | 25 | 45 | 78 | 95 | 100 | 100 |
| 5 | 15 | 38 | 55 | 80 | 96 | 100 | 100 | 100 | 100 |
| 10 | 30 | 65 | 83 | 97 | 100 | 100 | 100 | 100 | 100 |

Fig. 1

| Sample | Bacteria added (CFU/mL) | Bacteria found (CFU/mL) | Recovery (%) |
|---|---|---|---|
| **Rapid FTDI assay** | | | |
| River water 1 | 3,360 | 2839 (± 97) | 82-97 |
| River water 2 | 933 | 1030 (± 13) | 109-112 |
| River water 3 | 467 | 459 (± 38) | 93-109 |
| River water 4 | 233 | 232 (± 4) | 98-101 |
| River water 5 | 140 | 124 (± 3) | 86-91 |
| Apple juice 1 | 130 | 131 (±23) | 83-118 |
| Apple juice 2 | 130 | 122 (±2) | 93-95 |
| Apple juice 3 | 130 | 116 (±5) | 85-93 |
| Apple juice 4 | 130 | 133 (±19) | 88-117 |

Fig. 14

| Sample | Bacteria added (CFU/mL) | Bacteria found (CFU/mL) | Recovery (%) |
|---|---|---|---|
| | Ultrasensitive FTDI assay | | |
| River water 1 | 2.5 | 2.7 (±1.3) | 80-130 |
| River water 2 | 25 | 21.7 (±0.2) | 86-87 |
| River water 3 | 25 | 20.2 (±0.1) | 82-90 |
| River water 4 | 5 | 4.2 (±23) | 85-90 |

Fig. 19

| Method | Sample quantity | Sample Throughput | Time to Result | Detection Range (CFU/mL) | Wastes |
|---|---|---|---|---|---|
| PCR | Few µL | High Throughput | 3 h-30 h* | 10-100 CFU/mL | Low |
| Membrane Filtration | < 100 mL | Single Sample | 18-24 h | 1 CFU/unit | High |
| Most Probable Number Method | < 100 mL | Single Sample | 24-48 h | 1 CFU/unit | High |
| Lateral Flow Assays | > 500 µL | Single Sample | <30 min (12-20 h)* | $10^5$-$10^6$ | Low |
| ELISA Conventional | > 300 µL | High Throughput | 4-6 h | $10^3$-$10^6$ | Low |
| FTDI (This paper) | 10-100 mL | High Throughput | 2.5 -5.5 h | 0.7 CFU/mL | Low |

* Assays that use separate bacteria growth steps

Fig. 21

| Materials/reagents | Cost per plate ($) | Cost per well ($) |
|---|---|---|
| Filter -well plate | 20 | 0.21 |
| Antibodies | 5 | 0.055 |
| Blocking Agents | 7 | 0.07 |
| Substrate | 32 | 0.33 |
| Others | 1 | 0.01 |
| **Total** | 65 | 0.68 |

Fig. 22

| Sample | Bacteria added[1] (CFU/mL) | Bacteria found (CFU/mL) | Recovery (%) |
|---|---|---|---|
| River water 1 | 320 (± 20) | 290 (± 6) | 90-93 |
| River water 2 | 320 (± 20) | 351 (± 11) | 103-110 |
| Unfiltered river water | 320 (± 20) | 271 (± 43) | 71-98 |
| Pond water | 320 (± 20) | 322 (± 24) | 93-108 |

[a] The concentrations of bacteria and their standard deviation were estimated using the plate count agar method

Fig. 28

METHODS AND DEVICES FOR BACTERIA DETECTION USING FLOW PERMEABLE SENSORS

CROSS-REFERENCE TO RELATED APPLICATION

This patent document claims priority to earlier filed U.S. Provisional Patent Application Ser. No. 63/165,334, filed Mar. 24, 2021, the entire contents of which are incorporated herein by reference.

STATEMENT REGARDING FEDERALLY SPONSORED RESEARCH OR DEVELOPMENT

This invention was made with government support under Contract #W911QY-18-2-0006, awarded by the Dept. of the Army, US Army Combat Capabilities Development Command (DEVCOM) Soldier Center. The government has certain rights in the invention. Approved for Public Release PAO #PR2022_46758.

BACKGROUND OF THE INVENTION

1. Field of the Invention

The present patent document relates generally to devices and methods for detecting whole bacteria in liquid samples (e.g., water, beverages, juices etc.) or bacteria in liquid media derived from solid samples incubated in broth media; and, more particularly, to improved methods and devices capable of detecting down to a single bacterium in any volume of such a sample.

2. Background of the Related Art

Pathogenic bacteria (e.g., *Escherichia coli* O157:H7, *Staphylococcus aureus, Salmonella enterica, Campylobacter jejuni, Clostridium perfringens*, and Shiga toxin-producing *Escherichia coli*, etc.) pose a serious health threat to humans as their consumption can cause severe illness and even death. Studies attribute 4.8 million illnesses and 50,000 hospitalizations each year to pathogenic bacteria in the U.S. alone, while billions of illnesses and thousands of deaths occur from pathogenic bacterial infections in the rest of the world. Regulatory authorities (e.g., United States Environmental Protection Agency (US EPA), United States Department of Agriculture (USDA), etc.) require a number of products (e.g., drinking water, beverages, fruits, vegetables, raw meat, milk products, pharmaceuticals, etc.) to be tested and found free of pathogenic bacteria before being sold; therefore, billions of tests for detecting possible bacteria contamination are performed each year. Two methodologies, Membrane Filtration and Most Probable Number, are currently the most commonly used methods for detecting bacteria (both are accredited by US EPA and USDA). Both methods can achieve the required limit of detection (that is usually a single bacterium in 100 mL of sample), but they have the following disadvantages: (a) they are time-consuming (total analysis time being greater than 24 hours); (b) they can only identify the genus of the bacteria (while the specific strain is identified by using a molecular detection assay); (c) they require several consumables and produce large amounts of waste; and (d) sample throughput is typically low. Assays that can provide results in a few hours, can detect a very small number of bacteria in large sample volumes (ideally a single bacterium at 100 mL), and can analyze several samples simultaneously could find many applications in analytical and microbiology laboratories as well as quality control laboratories of several industries (e.g., food processing, biomanufacturing, etc.).

A variety of methodologies (e.g., enzyme-linked immunosorbent assay ("ELISA"), enzymatic methods, nucleic acid-based method, aptamer-based methods, lateral flow assays, etc.) and commercially available test kits (HybriScan Rapid Microbial Test System (Sigma-Aldrich), TRANSIA kits (Sigma-Aldrich)) can selectively detect bacteria in water, food, and environmental samples. These methodologies, however, cannot achieve the detection limits set by regulatory authorities and can only provide presumptive results. For example, commercially available ELISA kits for *E. coli* O157:H7 can detect bacteria in the range of $10^3$ to $10^6$ bacteria/mL using a 4-hour long analytical protocol. Previous research efforts have shown that the detection limit of ELISA assays can be improved by (a) combining a dual-antibody ELISA with HCR signal amplification or (b) by using nanomaterials to increase the analytical signal. The reported limits, however, are above the required limits set by regulatory authorities. Several lateral flow tests have been developed to detect specific strains of *E. coli, Salmonella typhimurium, Staphylococcus aureus*, and Cronobacter sakazakii and several impedimetric assays have detected *Escherichia coli* O157:H7, *Escherichia coli* ORN 178, and *Salmonella Typhimurium* among others. Paper-based devices to detect *Escherichia coli, Salmonella* spp., and *Listeria monocytogenes* by quantifying the β-galactosidase, phosphatidylinositol specific phospholipase C, or esterase bacterial enzymes have also been developed. The main limitation of the previously reported devices/assays is that they cannot achieve the very low detection limits (LOD) set by the regulatory authorities as their dynamic range is in the order of $10^3$-$10^7$ CFU ("colony forming units")/mL (LODs higher than 100 CFU/mL) that is far above the required detection limits (e.g., 1 CFU/100 mL for drinking water). One of the main reasons for the insufficient sensitivity of these assays is that they analyze small sample volumes, typically less than 0.5 mL. Few previous research studies have analyzed large sample volumes; mainly by filtering the samples through a syringe filter to capture the bacteria and then removing the membrane form the filter and detecting the trapped bacteria using conventional analytical techniques.

To detect a small number of bacteria in large sample volumes (ideally 100 mL) in a few hours is a challenging task because (i) the analytical assay should be ultrasensitive and be able to detect ideally a single live bacterium in the detection cell/area in few hours, and (ii) a large sample volume (up to 100 mL) should be analyzed. The majority of research efforts described in the literature have focused on the development of ultrasensitive assays, but they have overlooked the importance of the analysis of large sample volumes to get meaningful results. For example, when assays that analyze small sample volumes (e.g., less than 10 mL) give negative results, no safe conclusions can be reached whether the bulk sample is bacteria-free or bacteria are present in the bulk sample given the small volume tested. Actually, the smaller the volume of the tested volume is, the more dubious the conclusions that can be extracted from the results are. This is because the overall variance of a test results $s^2$ is given by $s^2=s_a^2+s_s^2$, where $s_a^2$ is the variance of the analytical procedure and $s_s^2$ the variance of the sampling operation. The $s_s^2$ is negligible for homogeneous samples that comprise analytes (i.e., small molecules, biomolecules, or ions) even at very small concentrations (e.g., picomolar levels) and for small sample volumes (e.g., 1 μL) because of the great number of molecules/ions in solution (e.g., 6.023×$10^5$/μL molecules in 1 pM solution). The results of the analysis of small sample aliquots are therefore good estimates of the true concentration of the tested analyte in the bulk sample. For samples that comprise small number of bacteria (<1 CFU/mL) in large volumes, however, the $s_s^2$ is significant and can dominate the overall variance. Assuming that the sampling of bacteria from large volumes is described by a hypergeometric distribution, then Table 1 (shown in FIG. 1) gives the probability (at 95% confidence level) three sample aliquots to comprise one bacteria vs. the aliquots volume and the number of bacteria in the bulk sample; we used three sample aliquots because samples are typically tested in triplicates and bulk sample volume equal to 100 mL because this is the volume of drinking water samples required to be tested by EPA standards. Table 1 shows, for example, that when the tested sample aliquot is 100 μL, then the probability that the three aliquots to comprise at least one bacterium is 26% when the bulk sample comprises 1 CFU/mL. On the contrary when the volume of each tested aliquot is 10 mL then the probability of sampling one bacterium is 83% when the bulk sample comprises 5 CFU/100 mL. The conclusions that can be extracted from the results of an analytical assay (even though this is ultrasensitive and can detect a single bacterium in the detection cell) are therefore related to the volume of the aliquot tested. For example, negative results of assays that analyze 100 μL aliquots can only suggest at best that the bulk sample does not comprise more than 10 CFU/mL. For assays that test 10 mL aliquots, negative results suggest at best that the bulk sample comprises not more than 10 CFU/100 mL. It is therefore clear that even presumptive assays that check for the presence of bacteria in samples (such as drinking water, foods, etc.), regardless of how sensitive they are, must analyze large sample volumes to extract meaningful conclusions.

SUMMARY OF THE INVENTION

This patent document discloses embodiments of devices and methods for the detection and concentration of bacteria in fluid samples. The embodiments of the sensor can detect whole live bacteria, dead bacteria, or fragments of bacteria. Furthermore, the devices and methods for the detection of bacteria may be configured and arranged to detect specific types of bacteria (e.g., *Escherichia coli, Staphylococcus aureus, Salmonella enterica, Campylobacter jejuni*, or *Clostridium perfringens*) or specific strains of bacteria, by way of example and not limitation. In one embodiment of a device for detecting bacteria the device includes one or more sensors, comprising one or more fluid-permeable sensing compartments, each having an inlet port, and an exit port for analyzing one or more samples of a fluid.

In addition to one or more of the above disclosed aspects, or as an alternate, the fluid-permeable sensing compartment(s) of the sensor can be made of plastic, glass, metal, or other polymeric material and can have the shape of a syringe filter, a microwell, a microcontainer, a filter-well plate, etc.

In addition to one or more of the above disclosed aspects, or as an alternate, the fluid-permeable sensing compartment of the sensor can comprise a filtration membrane, polymeric membrane, glass fiber membrane or any other fluid permeable structure that can allow liquids to pass through them and trap bacteria inside or on top of the structure.

In addition to one or more of the above disclosed aspects, or as an alternate, the fluid-permeable sensing compartment has sufficient size to comprise volumes from a few microliters to several milliliters when the inlet and/or exit ports of the fluid-impermeable detection compartment are tapped/closed.

In addition to one or more of the above disclosed aspects, or as an alternate, a solution or reagent can be added inside the fluid-permeable sensing compartment by using a syringe, a plastic tubing, a pipette, a dropper, or any other fluid delivery tool.

In addition to one or more of the above disclosed aspects, or as an alternate, the delivery of the solutions/reagents inside the fluid-permeable sensing compartment can be assisted by using pumps, automatic pipettes, multi pipettes, and the like.

In addition to one or more of the above disclosed aspects, or as an alternate, the drainage of fluid-permeable sensing compartments can be spontaneous, or assisted by using one or more of a vacuum manifold, a pump, a syringe, and the like.

In addition to one or more of the above disclosed aspects, or as an alternate, the sample may comprise a fluid, such as air or a liquid, that passes through a fluid-permeable sensing compartment.

In addition to one or more of the above disclosed aspects, or as an alternate, the sample may comprise a liquid sample comprising a liquid food sample or a beverage including water, juice, milk, and the like.

In addition to one or more of the above disclosed aspects, or as an alternate, the liquid sample can be a solution that is obtained after dipping/rinsing a solid food sample (leafy greens, meat, etc.) or a surface with a liquid.

In addition to one or more of the above disclosed aspects, or as an alternate, the liquid sample can be a solution that is obtained after incubating a solid food sample (leafy greens, meat, etc.) or a surface inside a bacteria growth media.

In addition to one or more of the above disclosed aspects, or as an alternate, liquid reagents may be added inside the fluid-permeable sensing compartment to perform an assay to determine the concentration of bacteria inside the tested sample.

In addition to one or more of the above disclosed aspects, or as an alternate, inside the fluid-permeable sensing compartment an immunoassay, an aptamer-based assay, or a nucleic acid-based assay may be performed to facilitate the determination of the concentration of bacteria in a sample.

In addition to one or more of the above disclosed aspects, or as an alternate, inside the fluid-permeable sensing compartment an immunoassay, an aptamer-based assay, or a nucleic acid-based assay produces a chemical product having a concentration that is related to the concentration of bacteria in a sample to thereby facilitate the determination of the concentration of bacteria in the sample.

In addition to one or more of the above disclosed aspects, or as an alternate, inside the fluid-permeable sensing compartment an immunoassay, an aptamer-based assay, or a nucleic acid-based assay produces a chemical product having a concentration that is related to the concentration of bacteria is a sample, wherein the concentration of the chemical product is performed inside the fluid-permeable sensing compartment by using an instrumental technique such as UV/VIS photometry, IR spectroscopy, fluorescence, luminescence, electrochemistry, and the like.

In addition to one or more of the above disclosed aspects, or as an alternate, inside the fluid-permeable sensing compartment an immunoassay, an aptamer-based assay, or a nucleic acid-based assay produces a chemical product having a concentration that is related to the concentration of bacteria is a sample, wherein the concentration of the chemical product is detected outside the detection compartment and inside a microwell; a cuvette; microtiter well plates that comprise electrodes; a microfluidic device; on top of a substrate that comprises reagents; on top of an electrode or electrode system such as screen-printed electrodes, an electrochemical cell, or fluid-permeable electrochemical cells; and the like.

Further disclosed is a sensing system comprising the sensor disclosed above which has one or multiple fluid-permeable sensing compartments, operatively coupled to a single channel or multichannel pump using plastic tubing to deliver samples and reagents into the fluid-permeable sensing compartments, operatively coupled to a vacuum manifold to allow the drainage of solutions from the fluid-permeable sensing compartments.

Further disclosed are methods of detecting bacteria in liquid samples by using the sensors disclosed above, comprising: obtaining a sample; passing the sample through the sensor; adding a first reagent to the sensor; letting the sensor with the reagent solution at a first predetermined temperature for a first predetermined time period; draining the first reagent from the sensor; washing the interior of the sensor with a liquid solution; adding a second reagent to the sensor; letting the sensor with the reagent solution at a second predetermined temperature for a second predetermined time period; draining the second reagent from the sensor; washing the interior of the sensor with a liquid solution; adding a third reagent to the sensor; letting the sensor with the reagent solution at a third predetermined temperature for a third predetermined time period; using a detector to measure the product produced during the immunoassay or aptamer-based assay to obtain an analytical signal that is related to the concentration of bacteria in the sample inside the sensor.

In addition to one or more of the above disclosed aspects, or as an alternate, the detection methods described above can have less or more steps where reagents are added, the sensor is let with a reagent solution at a predetermined temperature for a predetermined time period, and the reagent solution is drained from the sensor and the interior of the sensor is washed with a liquid solution.

Further disclosed is a sensing kit to detect bacteria in liquid samples by using the above disclosed methods. In an exemplary embodiment, the kit comprises a sensor having multiple flow-permeable sensing compartments, and with all necessary reagents.

In addition to one or more of the above disclosed aspects, or as an alternate, the sensing kit described above can also include a multi pipette, a 3D printed adapter that enlarges each well to host more sample volume, a single channel or multichannel pump and tubing, or a microplate vacuum manifold to allow high-throughput, parallel analysis of many samples.

Further disclosed is a portable sensing kit comprising the sensor disclosed above, containers with dry reagents that can be rehydrated just before use, syringes and droppers for sample and reagent delivery inside the sensor, caps to cover the inlet and outlet port of the sensor, one or more electrode systems that could be coupled to an electrochemical analyzer, and a container with a liquid solution.

Further disclosed is a method of detecting bacteria in liquid samples by using the portable sensing kit comprising: obtaining a sample; adding a liquid inside each container that has dry reagents to rehydrate the reagents, adding the sample in a syringe; connect the syringe to the inlet of the sensor and pass the sample through the sensor; adding a first rehydrated reagent to the sensor; capping the inlet and outlet ports of the sensors; incubating the sample at a first predetermined temperature for a first predetermined time period; draining the first reagent from the sensor; washing the interior of the sensor with a liquid solution; adding a second reagent to the sensor; capping the inlet and outlet ports of the sensors; incubating the sample at a second predetermined temperature for a second predetermined time period; draining the second reagent from the sensor; washing the interior of the sensor with a liquid solution; adding a third reagent to the sensor; incubating the sample at a third predetermined temperature for a third predetermined time period; pushing a small amount of the solution outside the sensor to come in touch with a electrochemical cell that is connected to an electrochemical analyzer; thereby determining via the analyzer the concentration of one or more products that are related to the concentration of bacteria in the sample; and graphing data representing the output of the potentiostat on the external device to thereby illustrate the concentration of bacteria in the sample.

In addition to one or more of the above disclosed aspects, or as an alternate, the detection method described above can have less or more steps where reagents are added, the sensor is let with a reagent solution at a predetermined temperature for a predetermined time period, and the reagent solution is drained from the sensor and the interior of the sensor is washed with a liquid solution.

In addition to one or more of the above disclosed aspects, or as an alternate, the detection method that would be used for analytical purposes could be fluorescence, UV/Vis spectrophotometry, or luminescence. For all these techniques a benchtop or a portable, battery-powered reader could be used.

Further disclosed is a method of detecting bacteria in liquid samples by using the portable sensing kit comprising: obtaining a sample; adding a liquid inside the containers that have the dry reagents to rehydrate the reagents, adding the sample in a syringe; connect the sample to the inlet of the sensor and pass the sample through the sensor; adding a first rehydrated reagent to the sensor; capping the inlet and outlet ports of the sensors; incubating the sample at a first predetermined temperature for a first predetermined time period; draining the first reagent from the sensor; washing the interior of the sensor with a liquid solution; adding a second reagent to the sensor; capping the inlet and outlet ports of the sensors; incubating the sample at a second predetermined temperature for a second predetermined time period; draining the second reagent from the sensor; washing the interior of the sensor with a liquid solution; adding a third reagent to the sensor; incubating the sample at a third predetermined temperature for a third predetermined time period; pushing some or all of the solution outside the sensor to a container; measure the optical properties (UV/VIS absorbance, fluorescence, luminescence) of the solution using a detector; and graphing data representing the output of the detector on the external device to thereby illustrate the concentration of bacteria in the sample.

BRIEF DESCRIPTION OF THE DRAWINGS

These and other features, aspects, and advantages of the present invention will become better understood with reference to the following description, appended claims, and accompanying drawings where:

FIG. 1 is an illustration of a Table 1 of the probability (%) of three sample aliquots comprising a single bacterium versus the aliquot volume and the concentration of bacteria in bulk sample;

FIG. 14 depicts a Table 2 showing recoveries of the analysis of spiked samples using rapid FTDI;

Figure 18B:
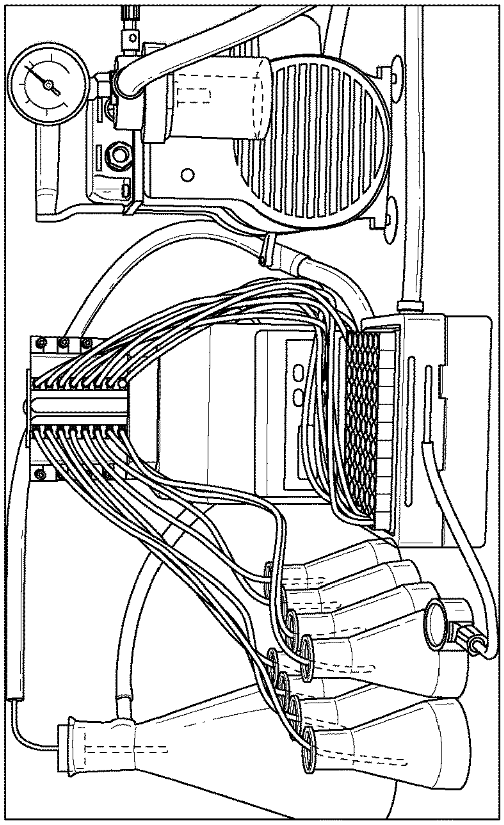
Figure 18A:
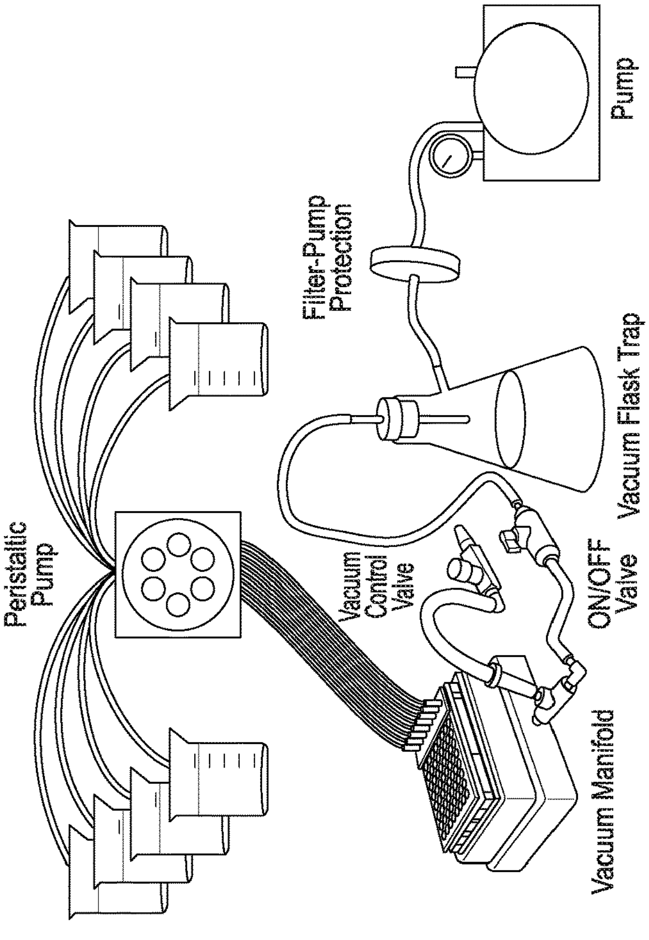
Figure 20A:
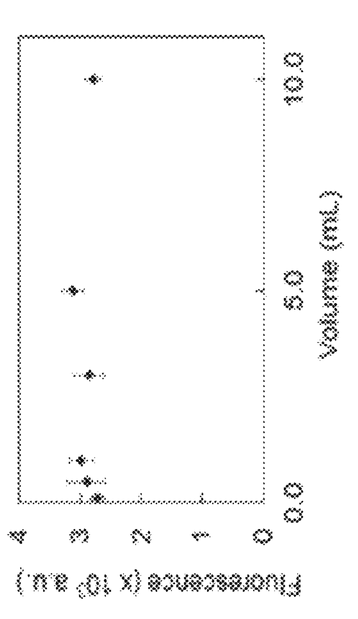
Figure 20B:
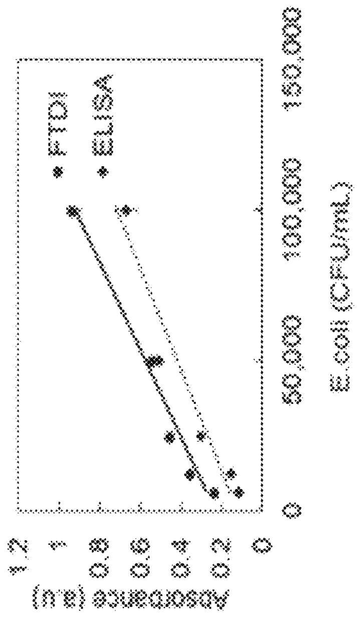
Figure 20C:
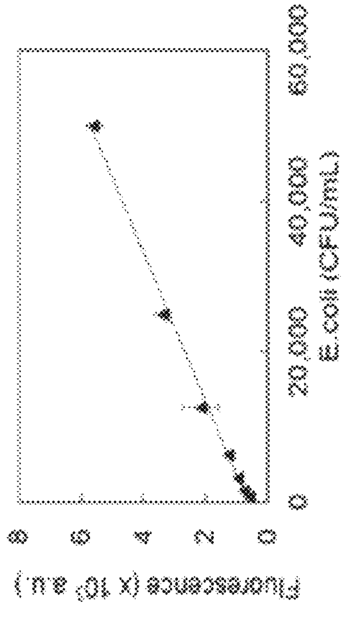
Figure 20D:
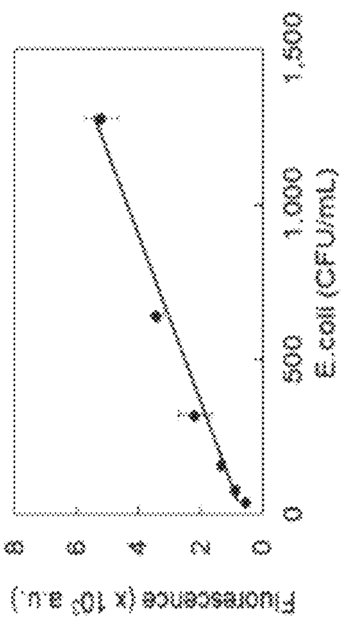
Figure 23:
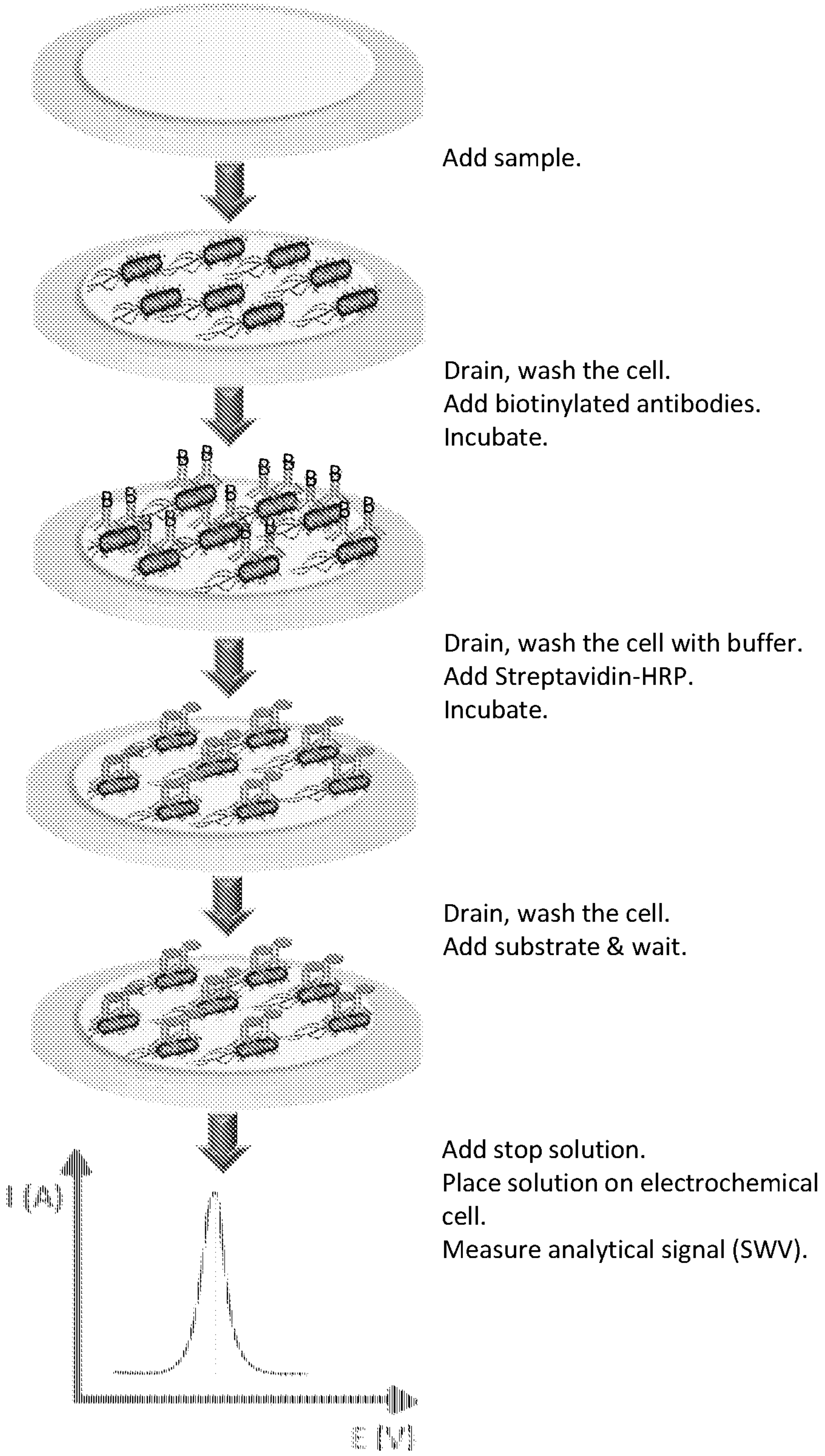
Figure 24:
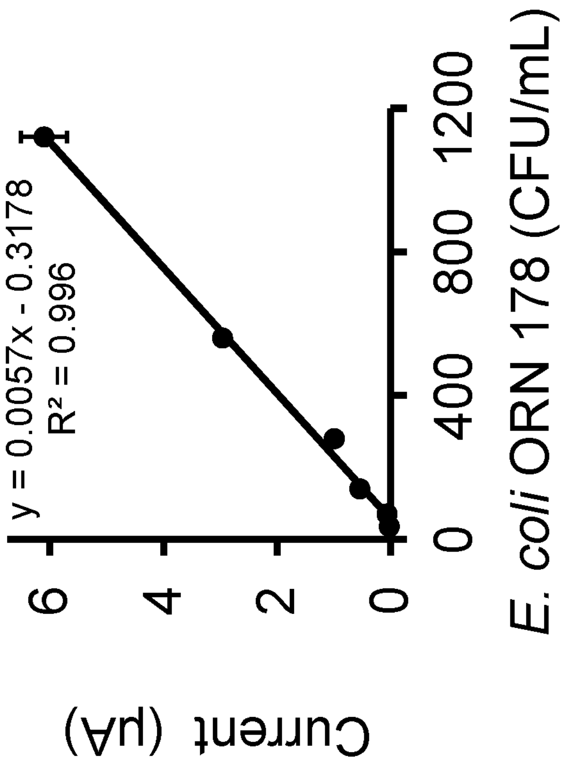
Figure 25:
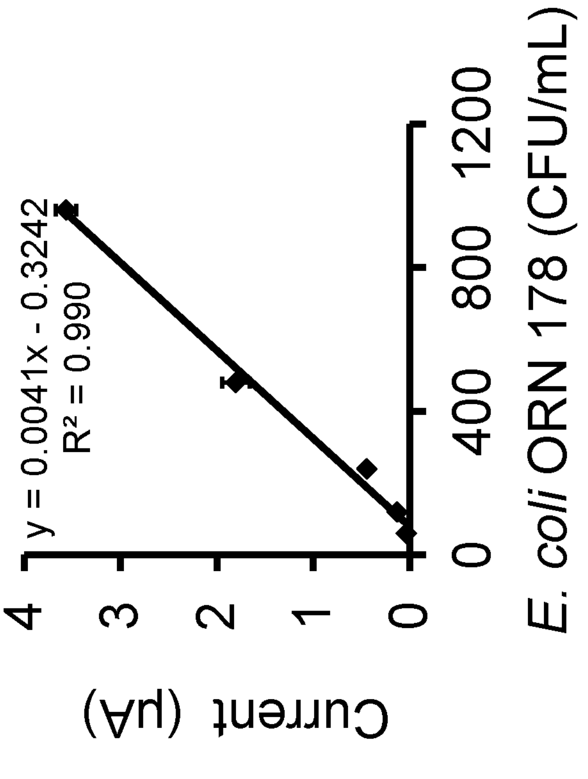
Figure 26:
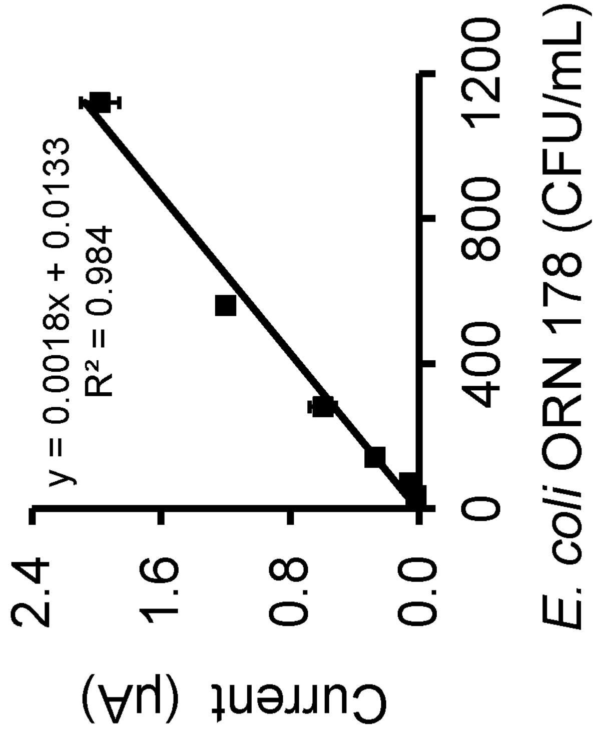
Figure 27:
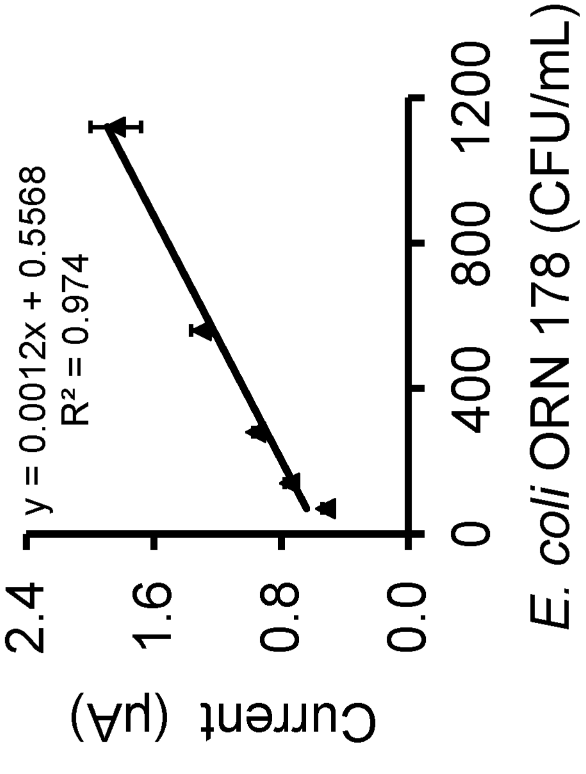
Figure 29A:
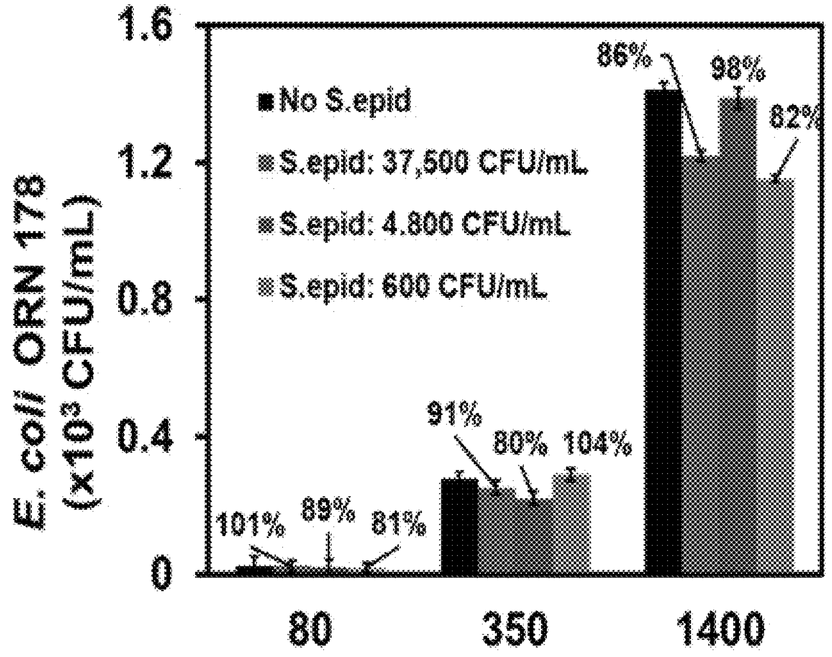
Figure 29B:
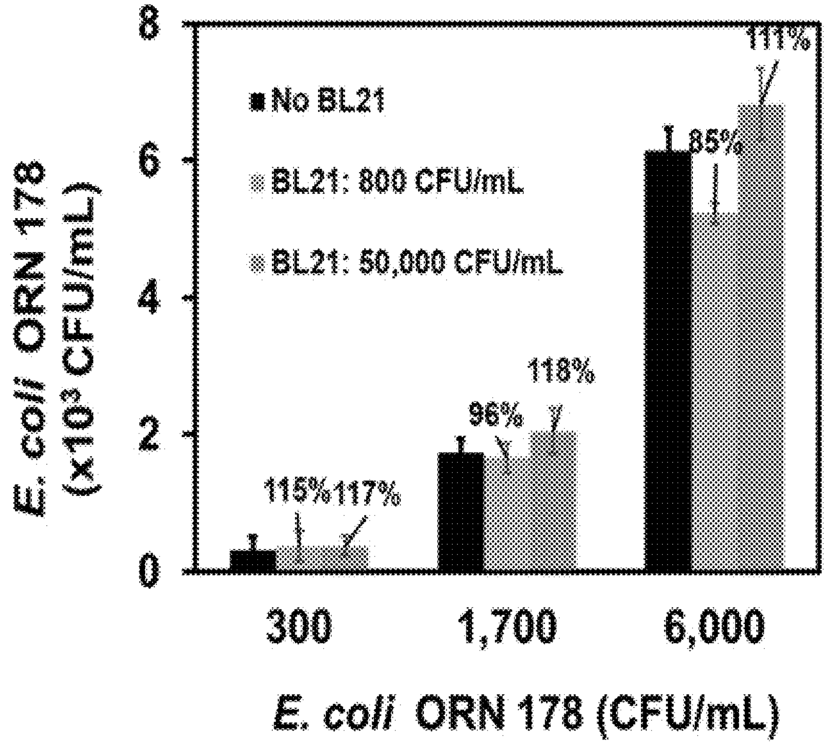
Figure 30:
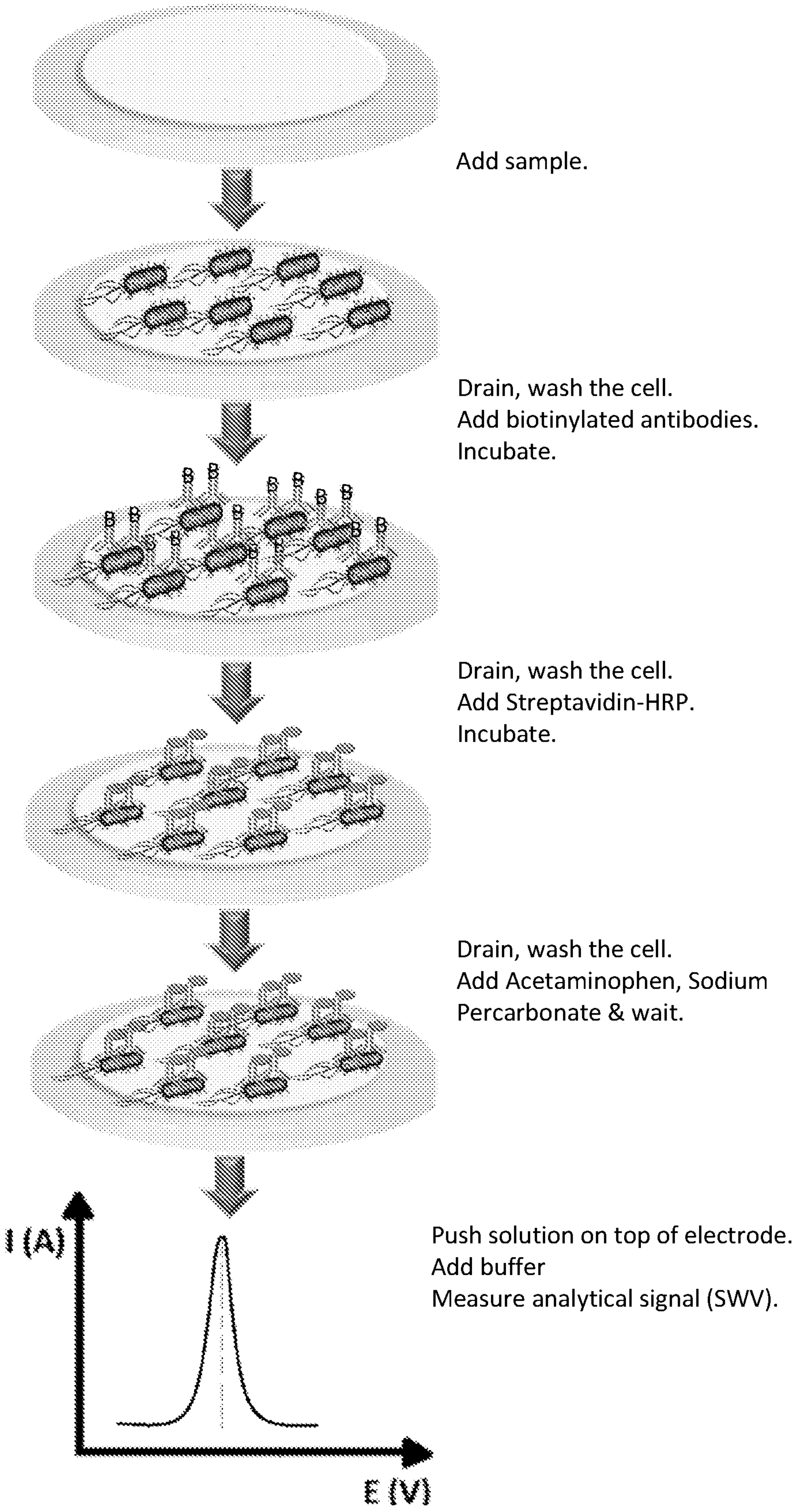
Figure 31:
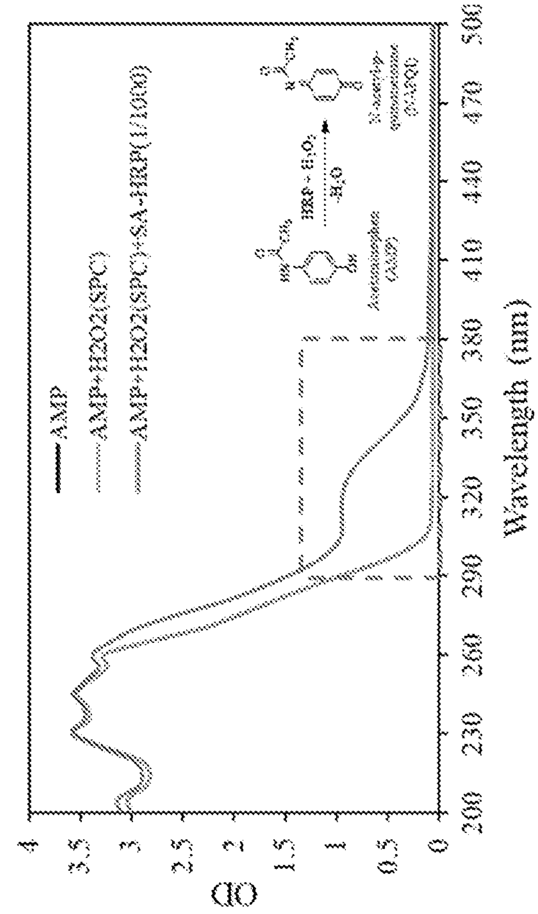
Figure 32B:
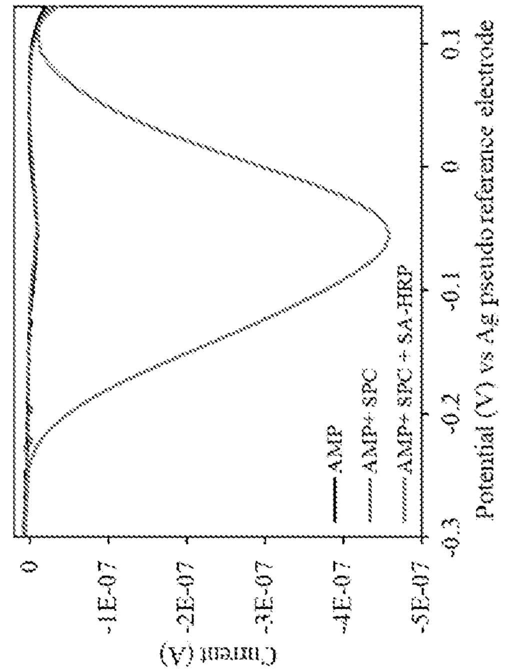
Figure 32A:
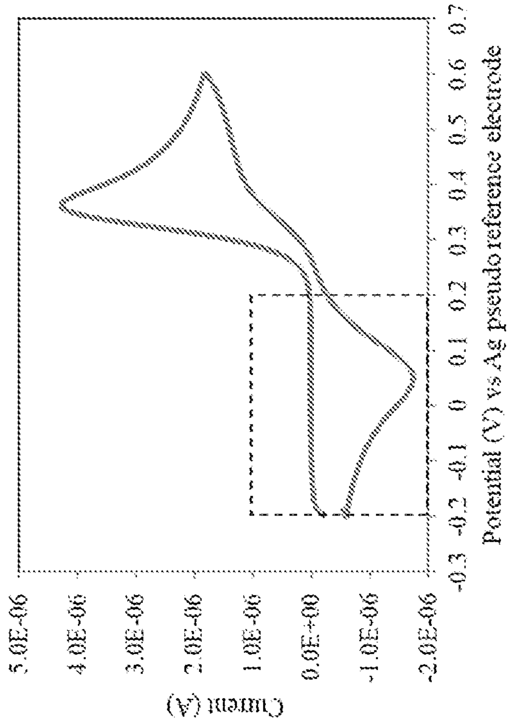
Figure 33:
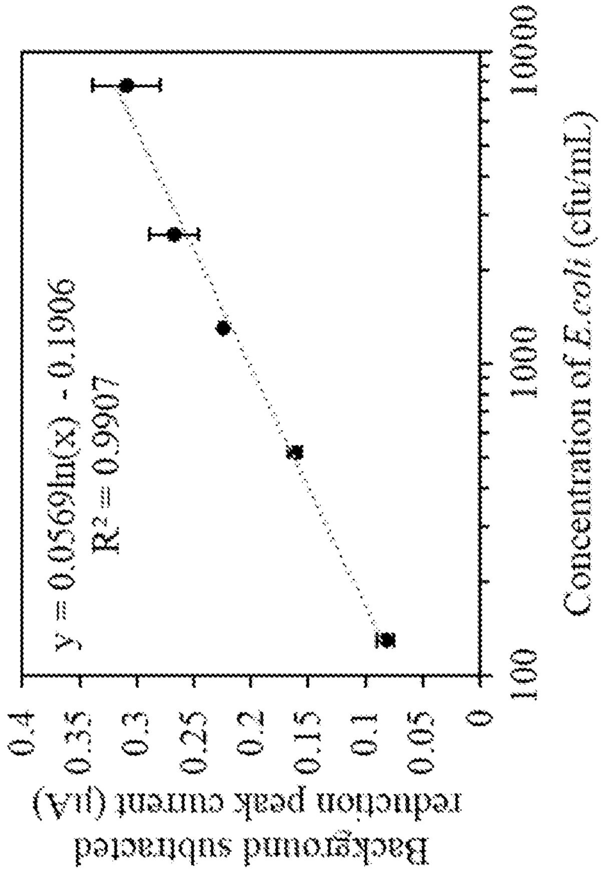
Figure 34:
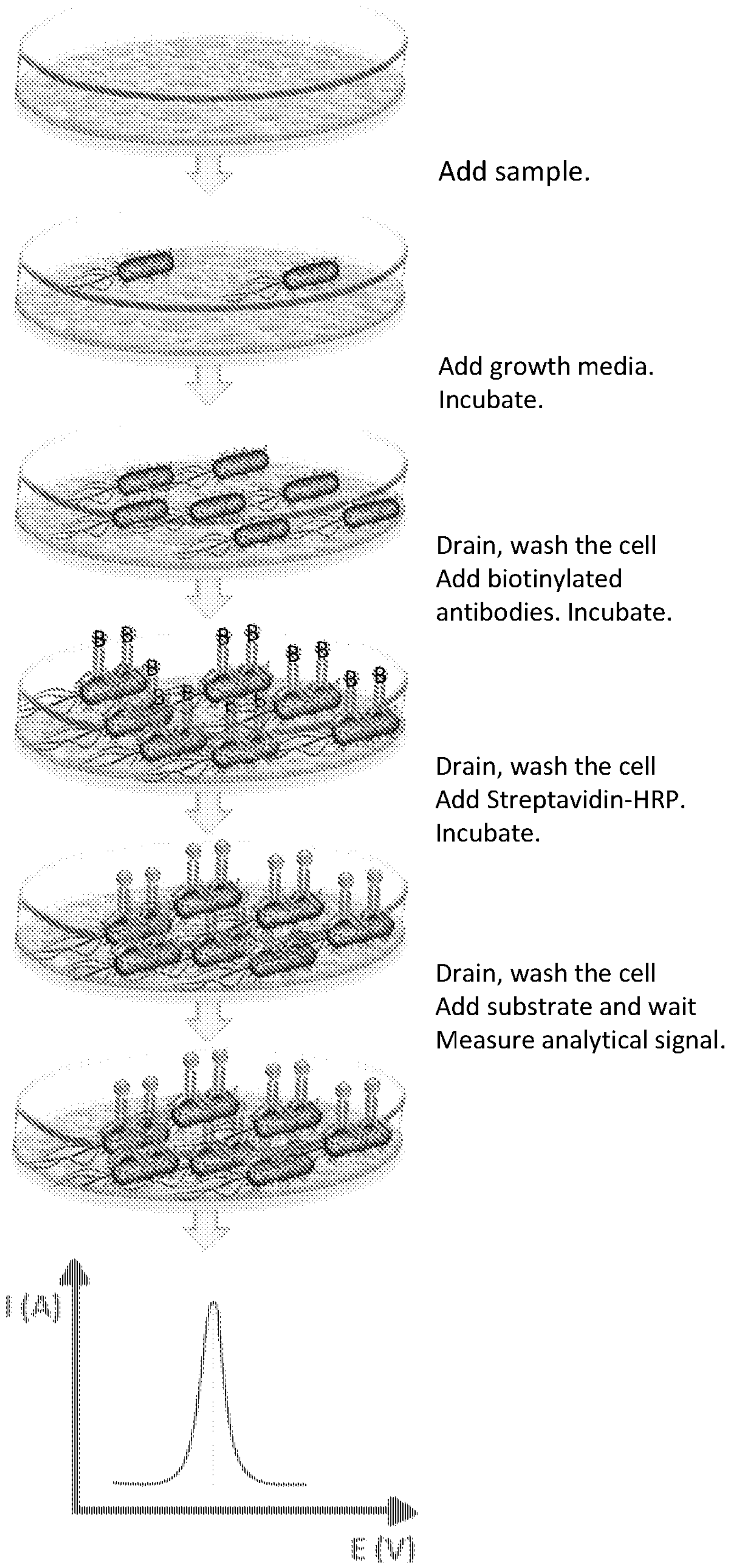
Figure 35:
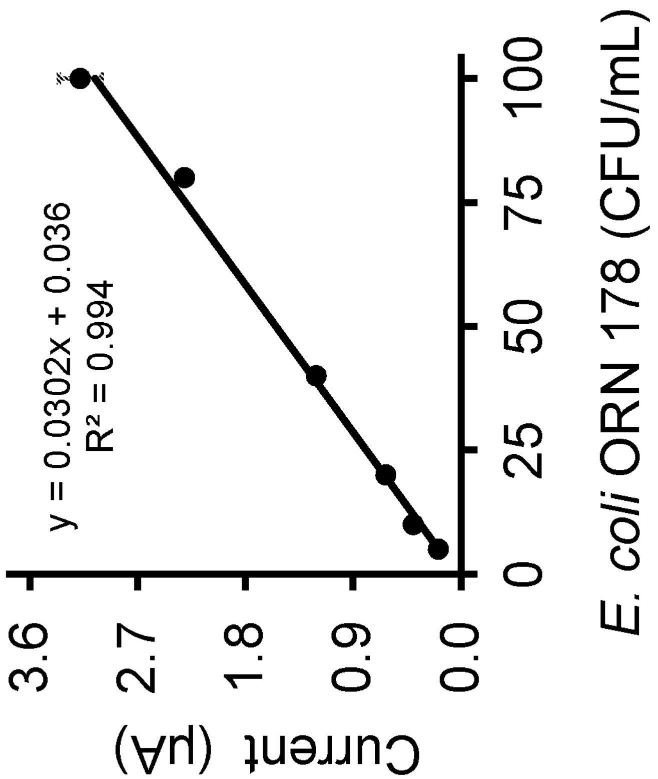
Figure 36:
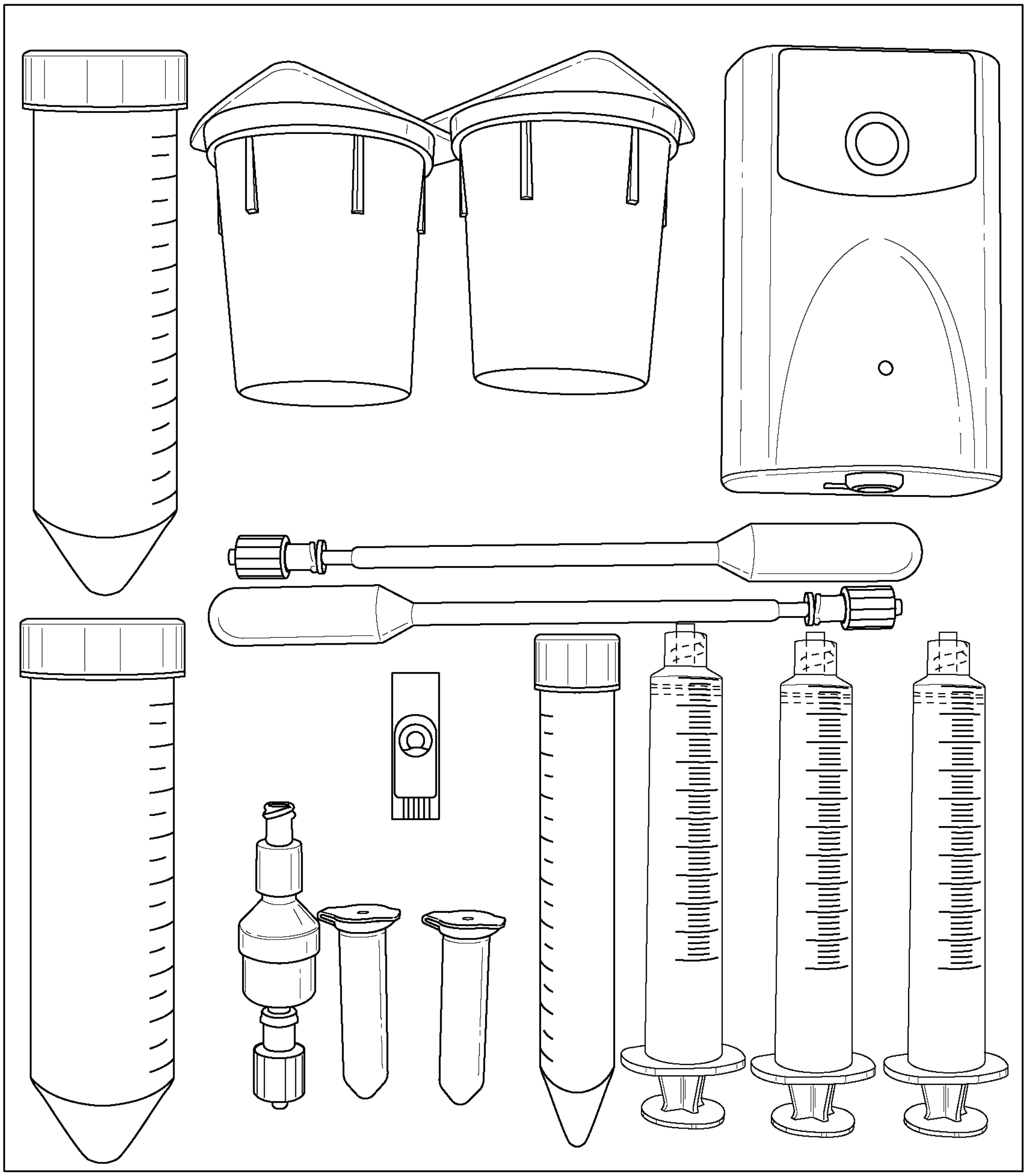
Figure 37:
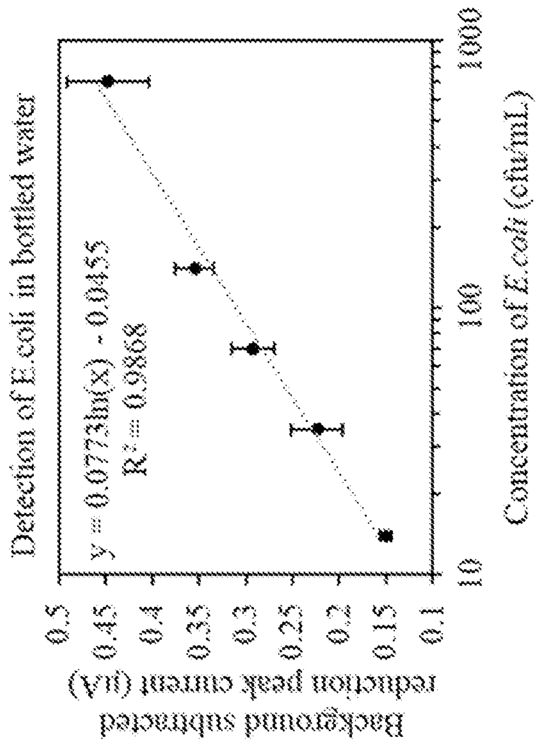
Figure 38:
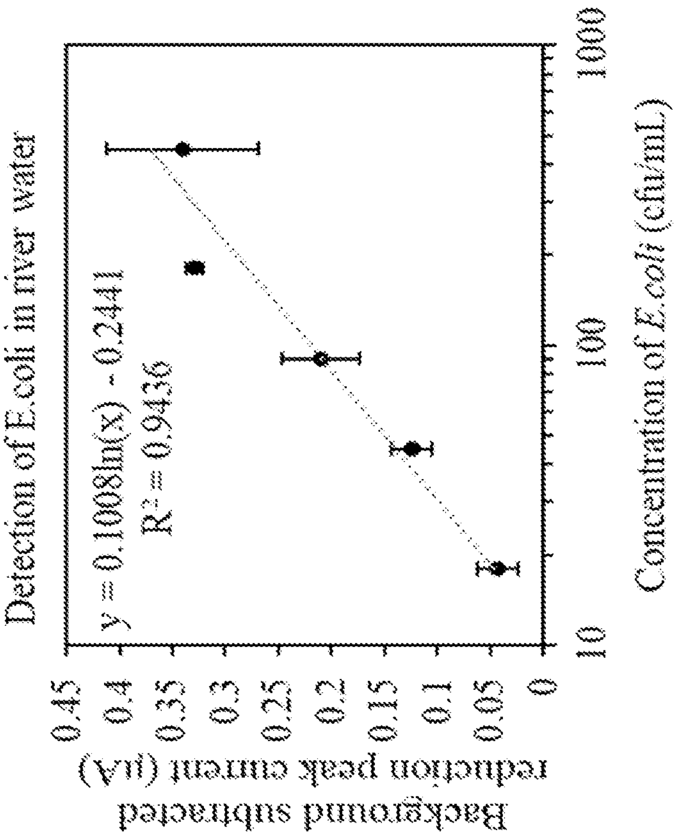
Figure 39:
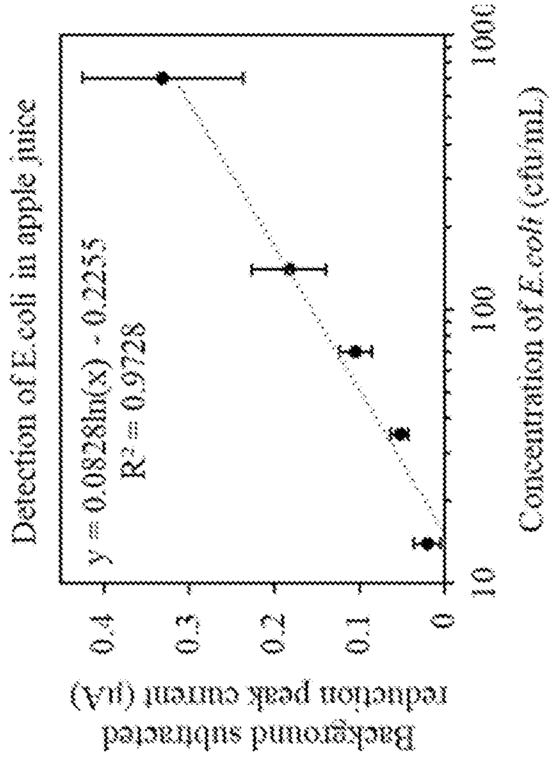
Figure 40:
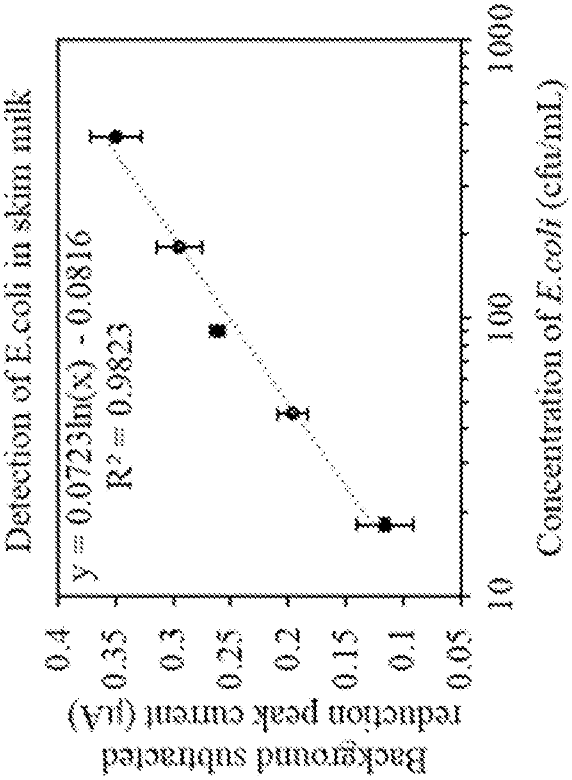
Figure 41:
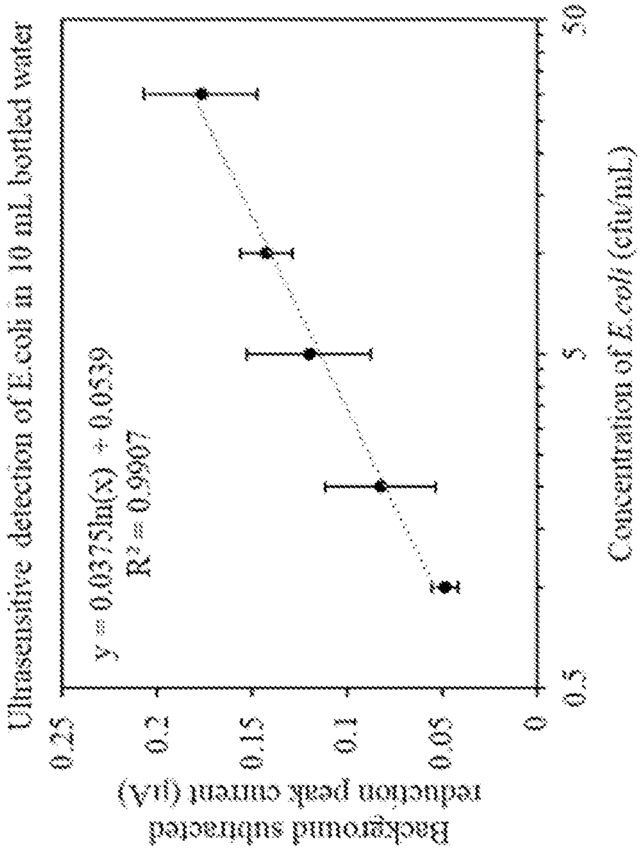
Figure 42:
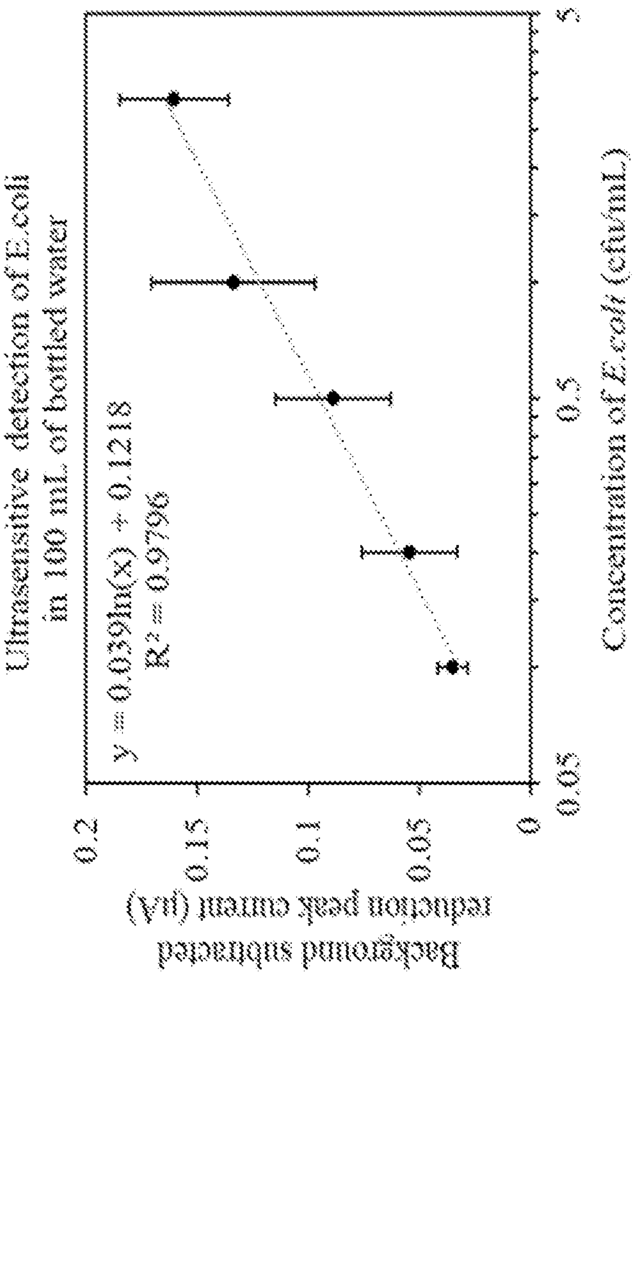

3 CFU/100 mL) when 100 mL of spiked spring water samples were analyzed with ultrasensitive FTDI assay;

FIG. 18A illustrates a schematic of the experimental set up suitable for the analysis of large sample volumes in parallel using a multichannel peristaltic pump and filter plate vacuum manifold, which has been used for the analysis 100 mL water samples contained in Erlenmeyer flasks and delivered to the wells using tubing;

FIG. 18B is a photograph of an exemplary experimental set up suitable for the analysis of large sample volumes in parallel using a multichannel peristaltic pump and filter plate vacuum manifold, which has been used for the analysis 100 mL water samples contained in Erlenmeyer flasks and delivered to the wells using tubing;

FIG. 19 depicts a Table 3 showing recoveries of the analysis of spiked samples using the ultrasensitive FTDI method;

FIG. 20A is an illustration showing the analytical signal of samples that have in total around 400 *E. coli* bacteria but in different sample volumes;

FIG. 20B is an illustration showing a calibration curve of spiked water samples analyzed with the rapid FTDI assay and a typical ELISA protocol in a standard microtiter well plate (in both cases the sample volumes were 100 μL and absorbance was used as detection technique);

FIG. 20C is an illustration showing a calibration curve of rapid FTDI for *E. coli* detection when the sample volume was 100 μL;

FIG. 20D is an illustration showing a calibration curve of the rapid FTDI method for *E. coli* detection when the sample volume was 5 mL;

FIG. 21 depicts a Table 4 comparing the characteristics of conventionally known methodologies for bacteria detection with those of the FTDI methods described herein;

FIG. 22 depicts a Table 5 showing the monetary costs of the FTDI for bacteria testing for a sensor with 96 sensing compartments (filter well plate) and for one single testing sample;

FIG. 23 is an illustration of a third exemplary method comprising the utilization of an electrochemical flow-through direct immunoassay ("electrochemical FTDI") where biotinylated antibodies and an enzyme conjugate are used for bacteria labeling, and a substrate reacts with the enzyme to produce an electrochemical product that is determined using an electrochemical technique;

FIG. 24 depicts a graph showing a calibration curve of peak current of square wave voltammograms of the products obtained from a method comprising electrochemical FTDI vs the concentration of *E. coli* when 10 mL of spiked deionized water were analyzed;

FIG. 25 depicts a graph showing a calibration curve of peak current of square wave voltammograms of products obtained from the electrochemical FTDI method vs the concentration of *E. coli* when 10 mL of spiked river water were analyzed;

FIG. 26 depicts a graph showing calibration curves of curves of peak current of square wave voltammograms of products obtained from the electrochemical FTDI method vs the concentration of *E. coli* when 10 mL of apple juice water were analyzed;

FIG. 27 depicts a graph showing calibration curves of curves of peak current of square wave voltammograms of products obtained from the electrochemical immunoassay FTDI method vs the concentration of *E. coli* when 10 mL of general test water were analyzed;

FIG. 28 depicts a Table 6 that shows the recoveries of the analysis of spiked real water samples using an electrochemical FTDI method;

FIG. 29A depicts a chart showing the results of specificity tests of the electrochemical FTDI method using different concentrations of *Staphylococcus epidermidis* as possible interferants, where the % *E. coli* (spiked)/*E. coli* (unspiked) is shown above each column;

FIG. 29B depicts a chart showing the results of specificity tests of the electrochemical FTDI method using different concentrations of *E. coli* BL21 as possible interferants, where the % *E. coli* (spiked)/*E. coli* (unspiked) is shown above each column;

FIG. 30 is an illustration of a fourth exemplary method including conducting an electrochemical FTDI assay where a growth media is used for bacteria proliferation, biotinylated antibodies and an enzyme conjugate are used for bacteria labeling, a substrate (acetaminophen) reacts with the enzyme to produce the electrochemical product (N-acetyl-p-quinoneimine), and an electrochemical record of the analytical signal is obtained;

FIG. 31 depicts a chart showing a UV-visible spectra of an acetaminophen solution without and with sodium percarbonate and streptavidin-HRP in a phosphate-buffered solution ("PBS") after a 10 minute incubation at room temperature;

FIG. 32A depicts a chart showing a cyclic voltammogram of the electrochemical redox reaction of 0.1 mM acetaminophen in PBS at a screen-printed carbon electrode;

FIG. 32B depicts a chart showing square wave voltammograms of acetaminophen after a 10 minute incubation without and with sodium percarbonate and streptavidin-HRP;

FIG. 33 depicts a chart showing calibration plots of the background subtracted currents of the square wave voltammograms of the products of the electrochemical FTDI method comprising the use of acetaminophen as a substrate vs the concentrations of *E. coli* spiked in 10 mL bottled water;

FIG. 34 is an illustration of a fifth exemplary method comprising the utilization of an ultrasensitive electrochemical flow-through direct immunoassay ("ultrasensitive electrochemical FTDI") where a growth media is used for bacteria proliferation, biotinylated antibodies and an enzyme conjugate are used for bacteria labeling, and a substrate reacts with the enzyme to produce an electrochemical product that is determined using an electrochemical technique;

FIG. 35 is a graph depicting a calibration curve of peak current of square wave voltammograms of products formed from the method depicted in FIG. 34 vs the concentration of *E. coli* when 10 mL of spiked water samples were analyzed;

FIG. 36 is a photograph of an embodiment of a portable sensing kit;

FIG. 37 is a chart depicting a calibration curve of peak current of square wave voltammograms of products produced in the portable sensing kit depicted in FIG. 36 vs the concentration of *E. coli* when 10 mL of spiked bottled water were analyzed;

FIG. 38 is a chart depicting a calibration curve of peak current of square wave voltammograms of products produced in the portable sensing kit depicted in FIG. 36 vs the concentration of *E. coli* when 10 mL of spiked river water were analyzed;

FIG. 39 is a chart depicting a calibration curve of peak current of square wave voltammograms of products produced in the portable sensing kit depicted in FIG. 36 vs the concentration of *E. coli* when 10 mL of spiked apple juice were analyzed;

FIG. 40 is a chart depicting a calibration curve of peak current of square wave voltammograms of products produced in the portable sensing kit depicted in FIG. 36 vs the concentration of *E. coli* when 10 mL of spiked skim milk were analyzed;

FIG. 41 is a chart depicting a calibration curve of peak current of square wave voltammograms of products produced in an ultrasensitive version of a portable sensing kit vs the concentration of *E. coli* when 10 mL of spiked bottled water were analyzed; and FIG. 42 is a chart depicting a calibration curve of peak current of square wave voltammograms of products produced in the ultrasensitive version of the portable kit vs the concentration of *E. coli* when 100 mL of spiked bottled water were analyzed.

DESCRIPTION OF THE PREFERRED EMBODIMENT

In a preferred embodiment of a device and method for the detection of bacteria in a fluid, a sensor is provided that may include one or more fluid-permeable sensing compartments that can hold a fluid-permeable structure and that is used to capture bacteria. In an exemplary embodiment, the fluid-permeable structure may include a filtration membrane, a polymeric membrane, a glass fiber membrane, or any other fluid permeable structure that can allow liquids to pass through them and that can trap bacteria inside or on top of the structure.

Figure 2D:
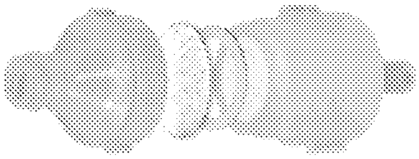
FIG. 2D is an illustration of the different parts of an embodiment of a sensor of FIG. 2C with one fluid-permeable sensing compartment having the shape of a syringe filter.
Figure 2C:
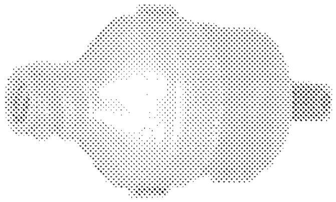
FIG. 2C is an illustration of another embodiment of a sensor with one fluid-permeable sensing compartment having the shape of a syringe filter.
Figure 2B:
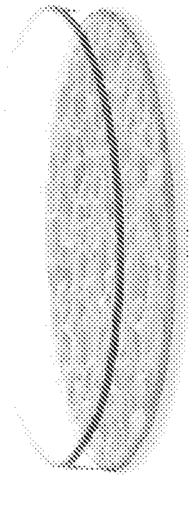
FIG. 2B is an illustration of another embodiment of a sensor with one fluid-permeable sensing compartment having the shape of a well with a membrane as its bottom.
Figure 2A:
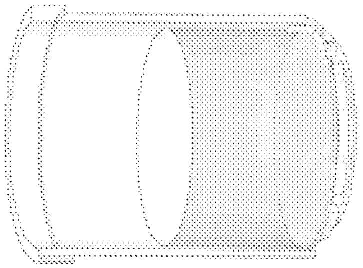
FIG. 2A is an illustration of an embodiment of a sensor with one fluid-permeable sensing compartment having the shape of a microwell with a membrane as its bottom.

Exemplary sensors having one fluid-permeable sensing compartment can have the shape of (a) a microwell with a fluid-permeable structure as its bottom (FIG. 2A), (b) a well with a fluid-permeable structure placed on its interior bottom side (FIG. 2B), and (c) a syringe filter that comprises a fluid-permeable structure disposed between an upper member and a lower member of the syringe filter (FIGS. 2C and 2D).

Figure 3B:
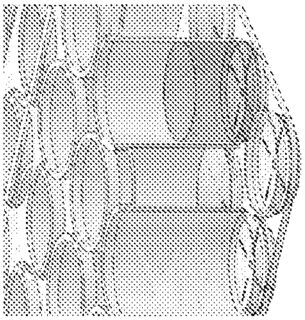
FIG. 3B is an illustration of a sensor that comprises a plurality of fluid-permeable sensing compartments, each being a microwell having a fluid-permeable structure at a bottom surface thereof, wherein the microwells are attached together to form an array of such microwells.
Figure 3A:
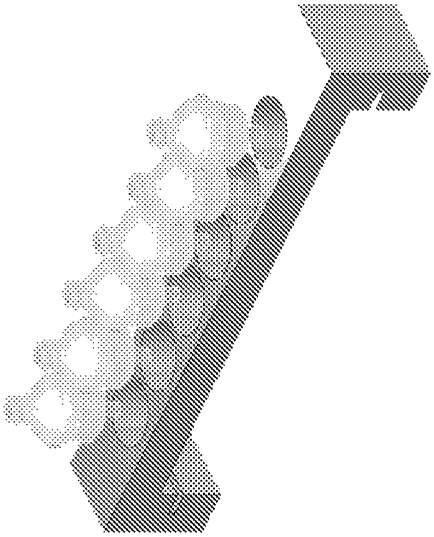
FIG. 3A is an illustration of a sensor having multiple fluid-permeable sensing compartments, each comprising a multiple syringe filter which includes a fluid permeable structure, wherein the sensing compartments are placed in a row with the aid of a holder.

Sensors having multiple fluid-permeable sensing compartments may comprise an array of sensors, each sensor of which may have a fluid-permeable sensing compartment. Such an exemplary sensor is depicted in FIG. 3A, wherein the senor comprises a plurality of syringe filters, each of which includes a fluid-permeable structure. The sensor further comprises a holder which is configured to receive the plurality of sensors. Another such exemplary sensor is depicted in FIG. 3B. The sensor in FIG. 3B comprises an array of microtiter wells with a membrane at the bottom of each well attached together to form an array of such wells like a filter well plate (FIG. 3B).

The fluid permeable sensing compartment of the sensor can be fabricated using various materials such as, but not limited to plastic, plastic composites, ceramics, ceramic composites, metals, metal composites, polymers, polymer composites, or a combination of one or more of these materials. The selection of material for the compartment of the sensors may vary widely but should take into consideration factors such as the target required for sensing; the reagents involved; storage conditions; environmental conditions; the settings in which the sensor is to be used such as field, research, or diagnostic lab settings, etc.; and the like.

The diameter and the exact dimensions of the fluid-permeable sensing compartment can be tailored based on the volume of the sample that is to be passed through the sensor, the volume of reagents that the sensor is to hold, the size or the type of the fluid-permeable structure required for the application, and the pressure or flow conditions required for the application based on the target, sample matrix, reagents, environmental conditions, etc.

The fluid-permeable structure of the sensor may comprise a filtration membrane, a polymeric membrane, a glass fiber membrane, or any other fluid permeable structure that can allow liquids to pass through them and that can trap bacteria inside or on top of a body of the fluid-permeable structure. The porosity of the fluid-permeable structure may be tailored (i.e., having porosity sized and dimensioned) to capture and retain the target bacteria.

The sensor may have an inlet port and an outlet port. Either or both of these ports may be configured to include connectors, such as, e.g., luer-lock design connectors, to allow tight attachment of a fluid delivery tool, such as, e.g., a syringe or a tubing, although other connection mechanisms may be used to attach a fluid delivery tool to the inlet and outlet ports of the sensor.

In an exemplary embodiment, a sensor having multiple fluid-permeable sensing compartments may include multiple inlet and outlet ports.

FIG. 3B demonstrates an exemplary embodiment of a sensor comprising multiple fluid-permeable sensing compartments, wherein each compartment has the shape of a 96-microtiter well plate. The fluid-permeable sensing compartment has a clear opening inlet from where the sample may be added. A fluid-permeable structure comprising a filtration membrane is disposed at the bottom of each well from where the solutions can be drained. Each well of a filter plate can hold up to about 300 microliters ("«L") of a solution, but higher volumes can be sampled as the wells can be drained from the bottom of the compartment via an outlet port.

The interior of the fluid-permeable sensing compartments may be treated with a reagent to hinder absorption or any type of non-specific binding of bacteria or reagents inside the fluid-permeable sensing compartments. For example, the compartments and the membranes can be pretreated by using proteins (e.g., bovine serum albumin), polymers (e.g., Polyvinyl alcohol) or any other commercially available blocking agents (e.g., SuperBlock™, Thermo Fisher Inc etc). The membranes and compartments can be pre-treated overnight with the blocking agents or compounds and then washed and air-dried as indicated for the pre-treatment blocking agent or compound.

Figure 4C:
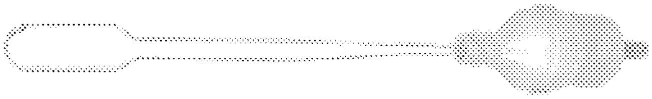
FIG. 4C is an illustration of an embodiment of a sensor having the shape of a syringe filter whose inlet is just below a dropper that can transfer a reagent/sample to the sensor.
Figure 4B:
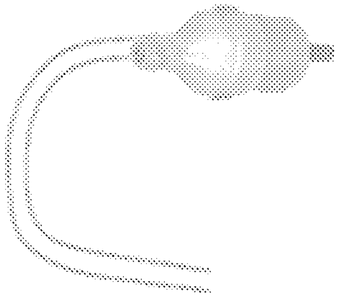
FIG. 4B is an illustration of an embodiment of a sensor having a tube for the transfer of a reagent/sample to the sensor.
Figure 4A:
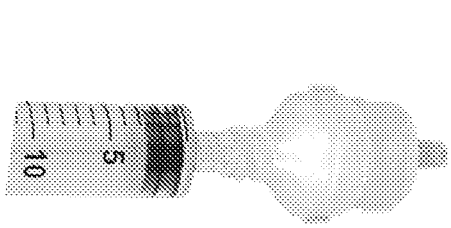
FIG. 4A is an illustration of an embodiment of a sensor configured and arranged to connect with a syringe for the delivery of a reagent/sample to the sensor.

FIG. 4 depicts an exemplary sensor having the shape of a syringe filter attached to exemplary delivery tools. As shown in FIG. 4A, the sensor may be connected to a syringe that comprises a sample or reagent. The syringe filter is well-suited to receive the syringe as the syringe filter has an inlet port that can attach to the syringe, and it has an outlet port that allows for the draining of the solution out from the sensor once the solution passes through the fluid-permeable structure of the sensor.

As shown in FIG. 4B, the sensor may be connected to a tube to thereby assist in the transfer of the sample to the sensor; and as shown in FIG. 4C, the sensory may be connected to a dropper that can add a sample/reagent into the fluid-permeable sensing compartment of the sensor.

A pump (such as a syringe pump, single-head peristaltic pump etc.) or any other device may be used to transfer the sample from a container holding the sample to the sensor.

Figure 5:
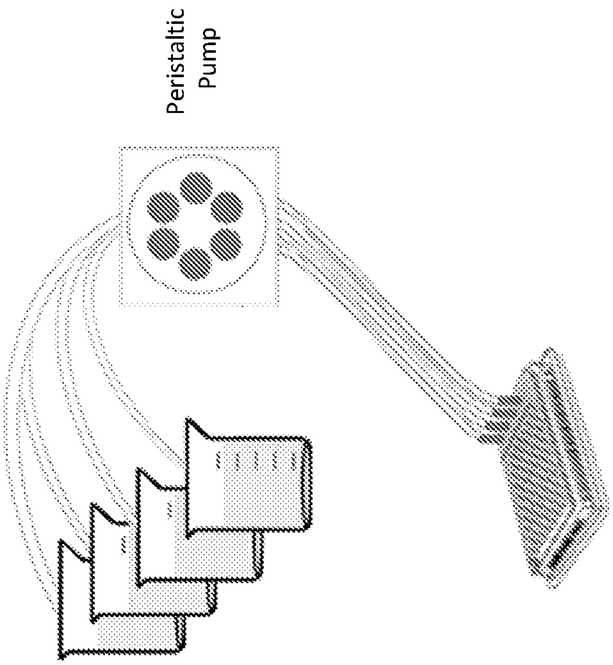
FIG. 5 is an illustration of an embodiment of a sensor with multiple fluid-permeable sensing compartments having the shape of a microwell, which are connected via tubes that can transfer samples/reagents from containers with the aid of a peristaltic pump.

Another exemplary sensor is depicted in FIG. 5. Here the sensor comprises a 96-microtiter filter well plate which has been adapted to be used as a sensor with fluid-permeable sensing compartments. The sample or reagents may be added inside the fluid-permeable sensing compartments from a top opening using a pipette or a dropper, using one or more tubing and a pump (FIG. 5), or any other fluid delivery tool that can transfer the solution to the well of the fluid-permeable sensing compartment.

The type of the fluid delivery tool that is appropriate for the addition of the solution to the fluid-permeable sensing compartment depends on the volume of the sample or reagent solution. For example, a pipette will be appropriate for adding a few microliters to several hundred microliters, a syringe will be appropriate for several hundred microliters to tens of milliliters, and a plastic tubing will be appropriate for tens of milliliters to several hundreds of milliliters or more.

Figure 6:
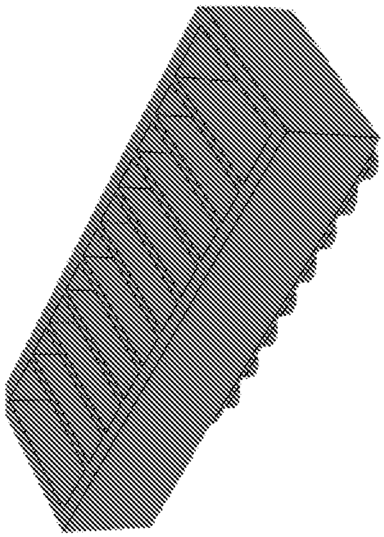
FIG. 6 is an illustration of an embodiment of a 3D printed adapter for connecting to an embodiment of a sensor having multiple filter microwells to enlarge the interior volume of the microwells to increase the total volume of sample/reagents that may be deposited in the microwells.

A 3D printed adapter that enlarges a number of wells of a sensor with multiple fluid-permeable sensing compartments (e.g., a filter well plate) can be used to host more sample volume and allow for the analysis of larger sample volumes. FIG. 6 shows an exemplary 3D printed adapter. The design of the adapter can be tailored based on the needed number and volume of wells.

Figure 7B:
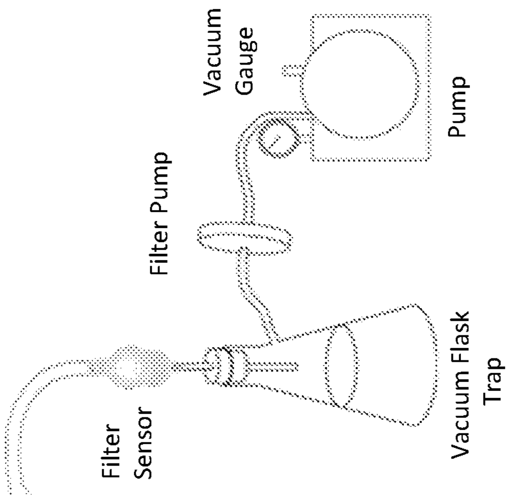
FIG. 7B shows an embodiment of a sensor having the shape of a syringe filter connected to vacuum system comprising a vacuum flask trap, a filter and a pump, where the vacuum system facilitates the draining of the reagents/samples from the sensor.
Figure 7A:
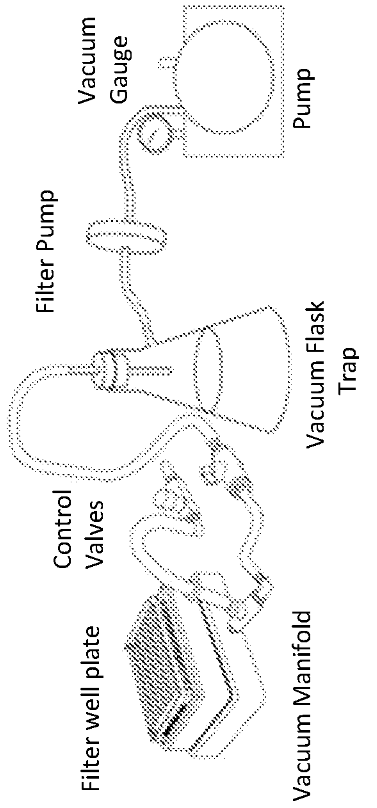
FIG. 7A shows an embodiment of a sensor with multiple fluid-permeable sensing compartments to be connected to a vacuum system comprising a vacuum manifold designed for filter well plates, a vacuum flask trap, a filter and a pump, where the vacuum system facilitates the draining of the reagents/samples from the sensor.

The fluid-permeable sensing compartment of the sensor can be drained spontaneously or by using a syringe fill with air that pushes the samples/reagents out of the compartment. A fluid-permeable sensing compartment of the sensor can be drained by using a vacuum system that facilitates the draining of the compartment. FIG. 7A shows the case where an exemplary vacuum system is used to drain the fluid-permeable sensing compartments of a multi-compartment sensor. FIG. 7B depicts an exemplary vacuum system that may be used to drain a fluid-permeable sensing compartment of a single-compartment sensor, such as, a syringe filter-configured sensor.

Figure 8:
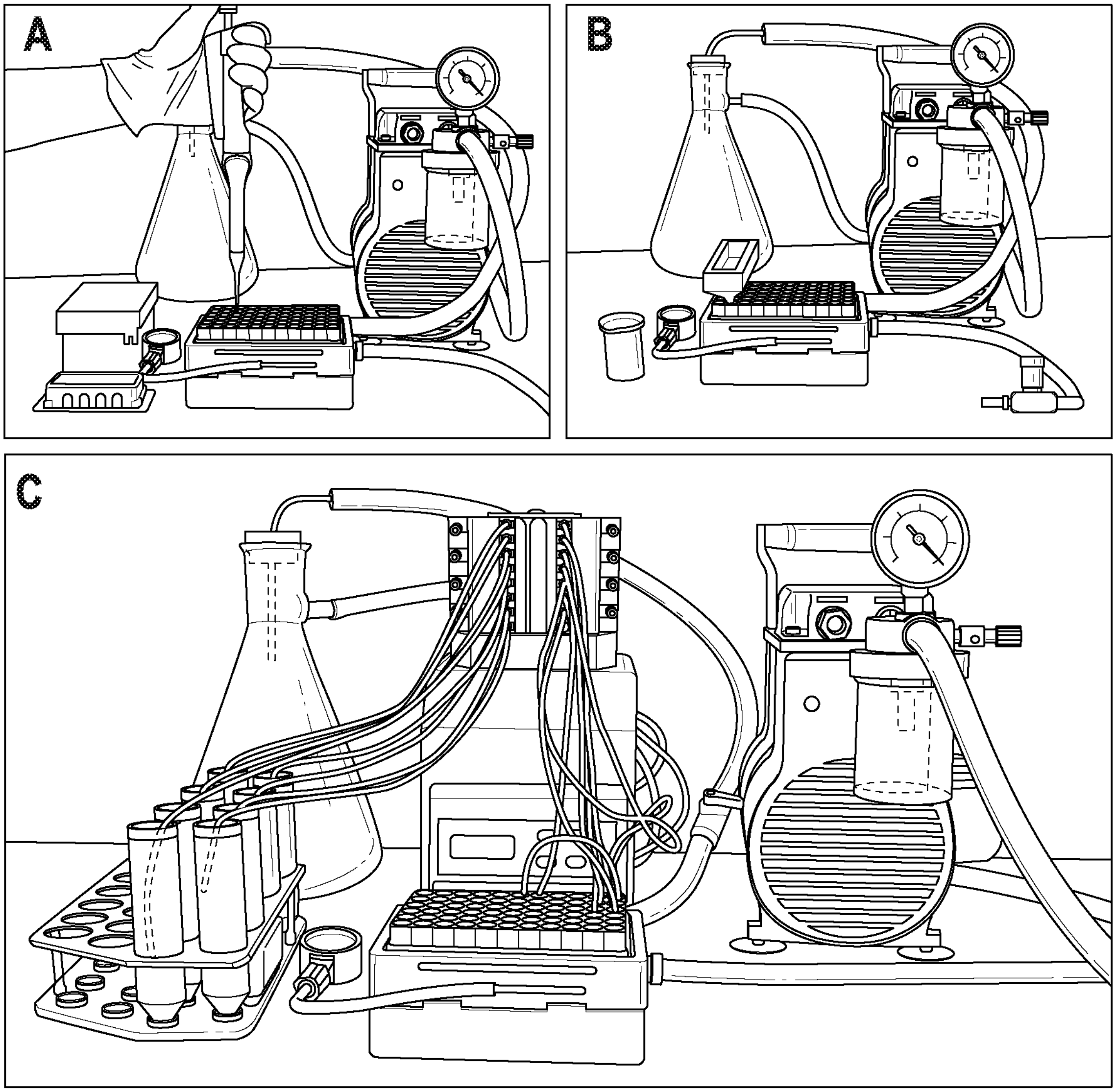
FIG. 8A is a photograph of an experimental setup that includes an embodiment of a sensor with multiple sensing compartments (that have the shape of a filter well plate) on top of a vacuum manifold to drain the sensing compartments while a multichannel pipet adds many samples in eight wells in parallel.
FIG. 8B is a photograph of an experimental setup that includes a 3D printed adapter of FIG. 6 attached to an array of sensing compartments of an embodiment of a sensor with multiple sensing compartments, where the sensor is on top of a vacuum manifold that facilitates the draining of the sensing compartments.
FIG. 8C is a photograph of an experimental setup that includes an embodiment of a sensor having multiple sensing compartments (that have the shape of a filter well plate) on top of a vacuum manifold to drain the sensing compartments, and further having a plurality of tubes to deliver a plurality of solutions from containers to the plurality of sensing compartments, respectively, of the sensor.

The sensor can analyze one or more samples, in series or in parallel. For example, as shown in an exemplary embodiment in FIGS. 8A, 8B, and 8C, eight samples can be analyzed in parallel if a sensor, having multiple fluid-permeable sensing compartments (e.g., a 96-well filter plate), is used with a vacuum system for draining the sensors and an eight-channel multipipette (FIG. 8A), a 3D printed adapter (FIG. 8B), or a multichannel pump and tubing (FIG. 8C).

Figure 9:
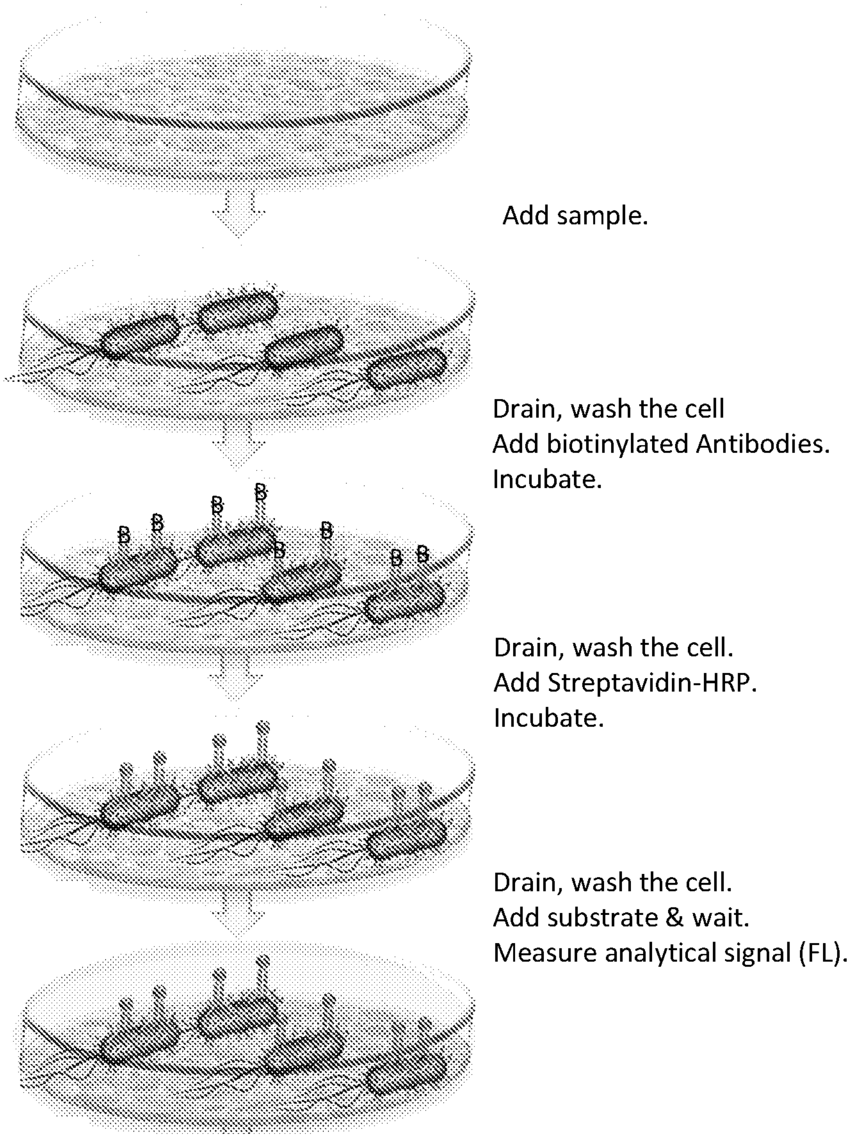
FIG. 9 is an illustration of a first exemplary method comprising the utilization of a rapid flow-through direct immunoassay ("rapid FTDI"). In this method, antibodies are used for bacteria labeling, an enzyme and a substrate are used for the production of a fluorescent product, and fluorescence is used as the analytical technique for recording the analytical signal.

Exemplary embodiments of methods for analyzing various volumes of samples using the sensors and/or systems disclosed above, shall now be discussed. A first method comprises a rapid flow-through direct immunoassay "rapid FTDI" that can analyze various volumes of samples ranging from a few microliters to hundreds of milliliters. The method can be performed in a sensor that comprises of one or more fluid permeable compartments. The method comprises an optional step of dipping/immersing the fluid permeable compartment(s), which comprises the casing/shell of the fluid-permeable sensing compartment and the fluid permeable structure, in a solution of a biomolecule that inhibits the non-specific analytical signal produced by antibodies, enzymes, etc. This dipping/immersion may be for a few minutes or several hours. Referring to FIG. 9, the method further comprises passing a collected sample through the fluid-permeable sensing compartment whereby the bacteria from the sample is captured by the fluid permeable structure, and the matrix is passed through the fluid permeable structure and is drained from the bottom of the fluid-permeable sensing compartment. Where the sensor has an inlet port and an outlet port, the draining of the cell may be facilitated by applying a negative pressure at the outlet port or by applying air at the inlet port. Once the cell has been adequately drained, and if the sensor has an outlet port, the outlet port may be covered. A reagent A may then be added to the fluid-permeable sensor compartment. The reagent A may comprise biomolecules such as antibodies raised against the bacteria (anti-bacteria antibodies), nucleic acids/aptamers specific to the bacteria (i.e., an aptamer sequence that binds to bacteria), antibodies against the bacteria that have been labeled with an enzyme (such as horseradish peroxidase (HRP), glucose oxidase (GOx), glucose dehydrogenase (GDH), tyrosinase (Tyr), alkaline phosphatase (ALP), β-galactosidase (β-gal)), a fluorescent molecule/particle (labeled anti-bacteria antibodies), aptamers against the bacteria that are labeled with an enzyme (such as HRP, GOx, GDH, Tyr, ALP, β-gal), and a fluorescence molecule/particle (aptamer sequence labeled with an enzyme or a fluorescence molecule/particle that binds to bacteria). After a waiting/incubation time that can be between a few seconds to many hours, the solution from inside of the fluid permeable sensing compartment may be drained and the compartment may be washed with a solution that may comprise salts and buffers, such as, e.g., a phosphate buffer saline, a phosphate buffer saline with a surfactant, a tris buffer, an acetate buffer, etc. If reagent A does not comprise labeled antibodies, another reagent may be added at a later step, wherein such reagent comprises one or more of enzymes (such as, e.g., HRP, GOx, GDH, Tyr, ALP, and β-gal) coupled to proteins (such as, e.g., avidin, streptavidin, and neutravidin) (e.g., streptavidin conjugated-HRP); enzymes (such as HRP, GOx, GDH, Tyr, ALP, β-gal) coupled to antibodies; enzymes (such as HRP, GOx, GDH, Tyr, ALP, and β-gal) coupled with aptamers; fluorescent molecules/particles coupled to antibodies; and fluorescent molecules/particles coupled to aptamers. The bottom of the cell may be covered, followed by a waiting period that may be between a few seconds to many hours, followed by another washing step with a liquid solution that may comprise buffers and surfactants. Another solution may then be added to the fluid-permeable sensing compartment, wherein such solution comprises compounds that can participate in enzymatic reactions, wherein such compounds include, e.g., chromogenic or fluorescent or redox active compounds such as 3,3',5,5'-tetramethylbenzidine (TMB), 3,3'-diaminobenzidine (DAB), o-phenylenediamine (OPD), 2,2'-azinobis [3-ethylbenzothiazoline-6-sulfonic acid] (ABTS), p-nitrophenyl phosphate (PNPP), o-nitrophenyl-β-D-galactopyranoside (ONPG), 10-Acetyl-3,7-dihydroxyphenoxazine (Amplex Red), acetaminophen, hydroquinone (HQ), and the like. The solution may further comprise oxidizing agents such as, e.g., hydrogen peroxide, sodium percarbonate, and the like. After a waiting period, a product is formed. Such a product may absorb into the UV/Vis range or the IR range, may emit fluorescence or luminescence, may participate into luminescence reactions, or may be redox active. The concentration of the product is related to the concentration of bacteria in the tested sample. This reaction product may be determined using an analytical technique, such as, e.g., UV/Vis photometry, fluorescence, luminescence, electrochemistry (e.g., amperometry, voltammetry, pulsed voltammetry, and square wave voltammetry) directly inside the fluid-permeable sensing compartment or outside of the compartment after having drawn out a portion of the reaction product from the compartment.

A representative example of the application of the rapid FTDI method lies in the detection of a model case bacteria (*E. coli* ORN 178) in 10 mL of a sample by using a sensor that has multiple flow-permeable sensing compartments (a 96-well filter plate having a membrane, DuraporePVDF, 0.45 um pore size, in the bottom of each microwell) and by using fluorescence as the analytical detection technique.

Scheme 1 (depicted in FIG. 9) shows the main steps of the assay. As shown, a sample is added/filtered into each microwell so that the bacteria present in the sample are trapped on top of the membrane and inside the microwell. In this example the sample volume analyzed in each fluid-permeable sensing compartment was 10 mL, but any other sample volume can be tested. The bacteria were detected using biotinylated anti-*E. coli* antibody (as detection antibodies), HRP conjugated with streptavidin (to label the detection antibodies), and Amplex Red and hydrogen peroxide (as an enzymatic substrate). The reaction of HRP with Amplex Red and hydrogen peroxide produces resorufin that can be detected using absorbance, fluorescence, or electrochemical measurements. Fluorescence detection ($\lambda_{ex}$, 540 nm and $\lambda_{em}$, 590 nm) is especially useful as the fluorescence of the solution in each well can be read inside the well (top-read measurement using a fluorescence plate reader).

An exemplary experiment protocol for this example comprises: add a sample (up to 10 mL) in a well of the filter well plate previously treated with Superblock™ in PBS; ash the well with 1 mL of PBST 0.05%; add 100 μL of 1 μg/mL solution of biotin-labeled *E. coli* antibody, and incubate for 1 hour with mild agitation at 37° C.; drain the well and wash it with 2 mL of PBST 0.05%; add 100 μL of HRP-Streptavidin solution and incubate for 20 minutes with mild agitation at 37° C.; drain the well and wash with 2 mL of PBST 0.05%; add 90 μL of substrate solution that comprise Amplex Red and hydrogen peroxide and incubate at 37° C. for 10 min; add 10 μL of stop solution and read the fluorescence ($\lambda_{ex}$: 540 nm, $\lambda_{em}$: 590 nm, top reading) within 30 min.

Figure 10A:
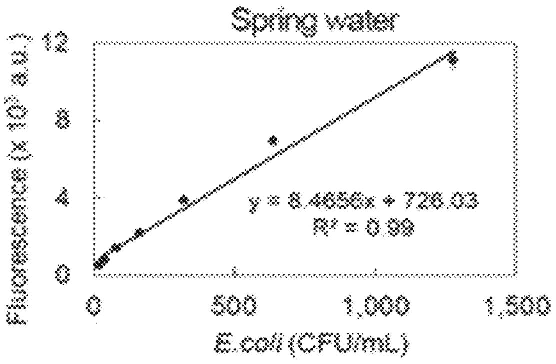
FIG. 10A is an illustration showing a calibration curve of fluorescence intensity of products of a method comprising rapid FTDI vs the concentration of *E. coli* when 10 mL of natural spring water were analyzed.
Figure 10B:
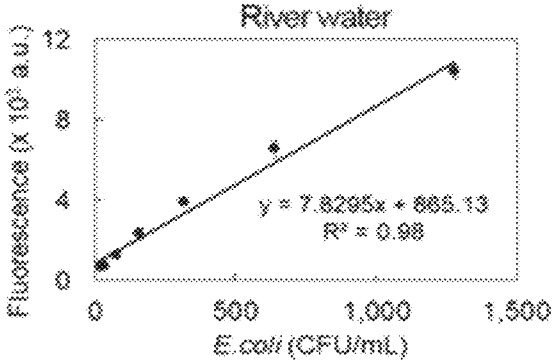
FIG. 10B is an illustration showing a calibration curve of fluorescence intensity of products of rapid FTDI vs the concentration of *E. coli* when 10 mL of river water were analyzed.
Figure 10C:
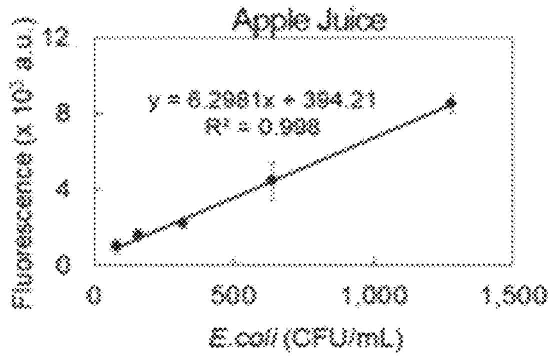
FIG. 10C is an illustration showing a calibration curve of fluorescence intensity of products of rapid FTDI vs the concentration of *E. coli* when 10 mL of apple juice were analyzed.

To evaluate the performance of the rapid FTDI method in the analysis of water and juice samples, calibration curves of the fluorescence signal of the assay mixture (after subtracting the fluorescence of the blank solutions) vs the concentration of bacteria in bottled water, river water, and apple juices all spiked with *E. coli* bacteria (FIGS. 10A, 10B and 10C), were prepared. A volume of 10 mL of samples was tested in all cases. It was concluded that the rapid FTDI assay can detect bacteria in levels as low as 17, 22, and 53 CFU/mL in the spring water, river water, and apple juice samples, respectively. The detection limits of the assays could be further improved by analyzing larger volumes of samples.

The intra-assay repeatability of the results of the rapid FTDI method measured by the average relative standard deviation (RSD) of triplicates at each concentration level was 5-6%. The relative standard deviation of results of the same samples analyzed on 3 different days ranged from 3-8%. Intra-assay repeatability up to 10-15% and inter-assay reproducibility up to 15-20% are satisfactory for immunoassays; therefore, the precision of assay meets acceptable performance standards.

Figure 11:
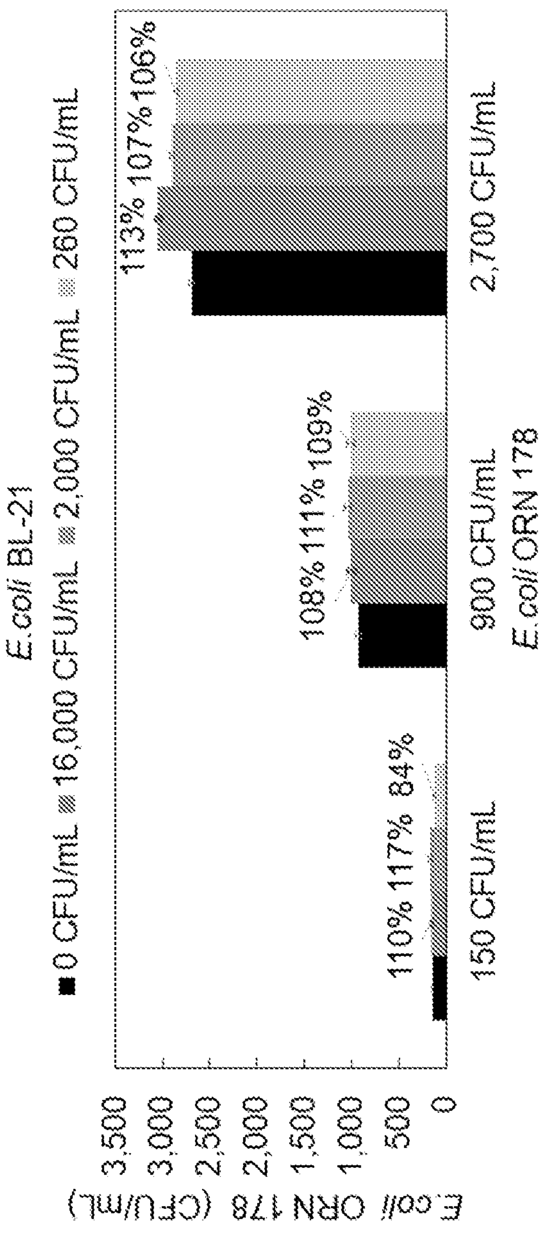
FIG. 11 shows a chart illustrating the results of selectivity tests for an embodiment of rapid FTDI using *E. coli* BL-21, wherein three concentration levels of *E. coli* BL-21 (260, 2000 and 16000 CFU/mL) were spiked in water samples comprising *E. coli* ORN178 in three concentration levels (150, 900, 2,700 CFU/mL), showing the percentage of the % recovery for each level.
Figure 12:
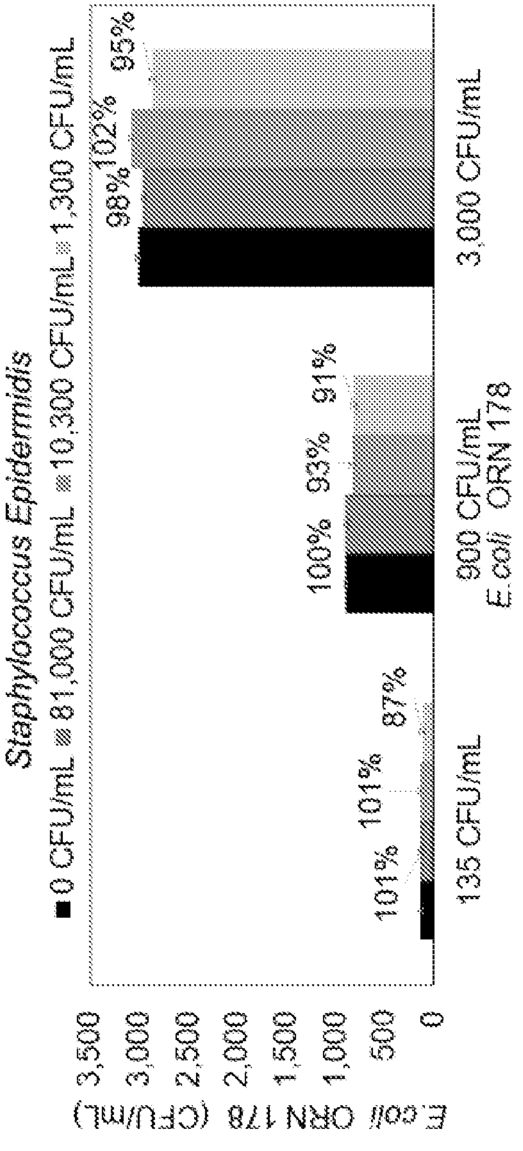
FIG. 12 shows a chart illustrating interference tests for the rapid FTDI using *Staphylococcus Epidermidis* (*S. Epid*), wherein three concentration levels of *Staphylococcus* (1,300, 10,300 and 81,000 CFU/mL) were spiked in water samples comprising *E. coli* ORN178 in three concentration levels (135, 900, 3,000 CFU/mL), showing the percentage of the % recovery for each level.
Figure 13:
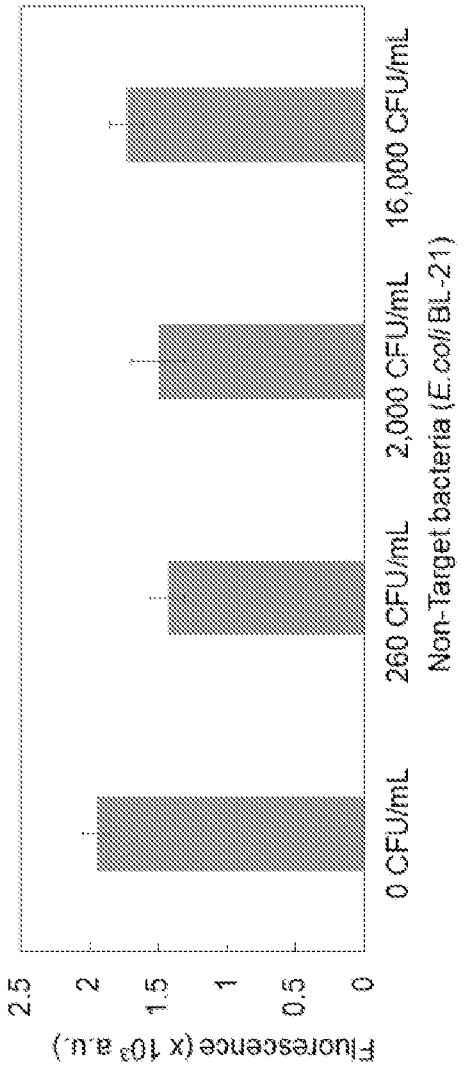
FIG. 13 shows a chart illustrating background fluorescence signals without the target bacteria and with the non-target bacteria *E. coli* BL-21 in concentrations 0, 260, 2,000, 16,000 CFU/mL.

The specificity of the rapid FTDI method was examined by testing whether the presence of nontarget bacteria influences the results of the assays for the determination of the targeted *E. coli* bacteria. One Gram-positive strain, *Staphylococcus epidermidis* (ATCC 35984) and a Gram-negative strain *E. coli* BL21 were the nontarget bacteria used in these tests. *E. coli* BL21 have no O- or K-antigens in their cell surface and so they should not cross react with the *E. coli* serotype O/K antibodies used in the assays. Standard solutions of *E. coli* ORN178 that contained *E. coli* at three different concentration levels were spiked with solutions containing the nontarget bacteria at three different concentration levels. The obtained samples were then analyzed using the rapid FTDI assay method described above. The concentration of the target *E. coli* ORN178 levels in the solutions spiked with nontarget bacteria was calculated using the calibration curve prepared with standard *E. coli* solutions. The spiked solutions were also tested using the plate count agar assay. The percent recoveries were calculated from the % ratio of *E. coli*$_{(spiked)}$/*E. coli*$_{(unspiked)}$. The results of the specificity tests suggest that non target bacteria do not interfere with the detection of the target bacteria because the percent recoveries are close to 100% (FIGS. 11, 12) and the fluorescence signals (mean values and standard deviations) of the blank solutions and the samples that contained no-target bacteria were similar (FIG. 13).

To assess the accuracy of the rapid FTDI assay, we performed recovery experiments in apple juice and in real river water samples. Apple juice and river water samples were first spiked with *E. coli* bacteria, and then 10 mL of aliquots of them were analyzed with the FTDI assays. Recovery experiments were performed using spiked river water samples and spiked apple juice samples. The exact number of bacteria in each spiked sample was also determined using the plate agar count assay. The spike recovery was calculated as the % ratio of (*E. coli*$_{added}$-*E. coli*$_{found}$)/*E. coli*$_{added}$. The recoveries of the results of the rapid FTDI assays are shown in Table 2 (see FIG. 14) and found to range from 82 to 118%. Mean recovery values between 70 and 120% with a relative standard deviation of less than 20% are considered acceptable for the nature of these experiments.

Another method for detecting bacterial concentrations comprises an ultrasensitive flow-through direct immunoassay ("ultrasensitive FTDI method"). The ultrasensitive FTDI method can analyze various volumes of samples ranging from a few microliters to hundreds of milliliters and can detect very small concentrations of bacteria as low as less than 1 CFU/mL. This method can be performed in sensors that comprise of one or more fluid-permeable sensing compartments. An exemplary ultrasensitive FTDI method comprises: passing a collected sample through a fluid-permeable sensing compartment having a fluid permeable structure positioned within a cell of the compartment, wherein the structure is selected such that the bacteria from the sample are captured by the fluid-permeable structure, and the matrix passes through the fluid-permeable structure and is drained from the bottom of the cell. The draining of the cell may be facilitated by applying a negative pressure at the outlet port or by applying air at the inlet port. Following that, the outlet port of the sensor may be covered. The method further comprises adding a liquid reagent that may comprise a growth media (e.g., lysogeny broth (LB) media, etc.) to the fluid-permeable sensing compartment to facilitate the proliferation of bacteria. Following the addition of the reagent that may comprise a growth media, there would be a waiting/incubation time that can be between few seconds to many hours, at a temperature range between 5° C. to 50° C. Following the waiting/incubation time, the solution from the inside of the fluid-permeable sensing compartment is drained and the compartment is washed with a solution that may comprise salts and buffers such as, e.g., phosphate buffer saline, phosphate buffer saline with a surfactant, tris buffer, acetate buffer, etc. In the consequent step, a reagent that may comprise biomolecules is added to the fluid-permeable sensing compartment. The biomolecules may include, e.g., antibodies raised against the bacteria (anti-bacteria antibodies), nucleic acids/aptamers specific to the bacteria (aptamer sequence that binds to bacteria), antibodies against the bacteria that have been labeled with an enzyme (such as, e.g., HRP, GOx, GDH, Tyr, ALP, β-gal, etc.) or a fluorescent dye (labeled anti-bacteria antibodies), aptamers against the bacteria that are labeled with an enzyme (HRP, GOx, GDH, Tyr, ALP, β-gal, etc.) or a fluorescence dye (aptamer sequence labeled with an enzyme or a fluorescence dye that binds to bacteria). After a waiting/incubation time that can be between few seconds to many hours, at the desired temperature, the solution from the inside of the fluid-permeable sensing compartment is drained and the compartment is washed with a solution that may comprise salts and buffers, such as, e.g., phosphate buffer saline, phosphate buffer saline with a surfactant, tris buffer, acetate buffer, etc. If the solution comprises non-labeled antibodies, a solution comprising a reagent such as enzymes (such as, e.g., HRP, GOx, GDH, Tyr, ALP, β-gal, etc.) coupled to proteins (e.g., streptavidin conjugated-HRP, etc.), enzymes (such as, e.g., HRP, GOx, GDH, Tyr, ALP, β-gal, etc.) coupled to antibodies, enzymes (such as HRP, GOx, GDH, Tyr, ALP, β-gal, etc.) coupled with aptamers, fluorescent molecules/particles coupled to antibodies, fluorescent molecules/particles coupled to aptamers, and the like, would be added, after covering the bottom of the cell, followed by a waiting period that may be between few seconds to many hours, followed by another washing step with buffers. Lastly, a solution that comprises compounds (chromogenic or fluorescent or redox active compounds such as TMB, DAB, OPD, ABTS, PNPP, ONPG, Amplex Red, HQ, etc.) that can participate in enzymatic reactions and oxidizing agents (such as hydrogen peroxide, sodium percarbonate etc.) are added to the fluid-permeable sensing compartment. After a waiting period, a product is formed. Such a product may absorb into the UV/Vis range or the IR range, may emit fluorescence or luminescence, may participate into luminescence reactions, or may be redox active. The concentration of the product is related to the concentration of bacteria in the tested sample. This reaction product may be determined using an analytical technique, such as, e.g., UV/Vis photometry, fluorescence, luminescence, electrochemistry (e.g., amperometry, voltammetry, pulsed voltammetry, and square wave voltammetry) directly inside the fluid-permeable sensing compartment or outside of the compartment after having drawn out a portion of the reaction product from the compartment.

Figure 15:
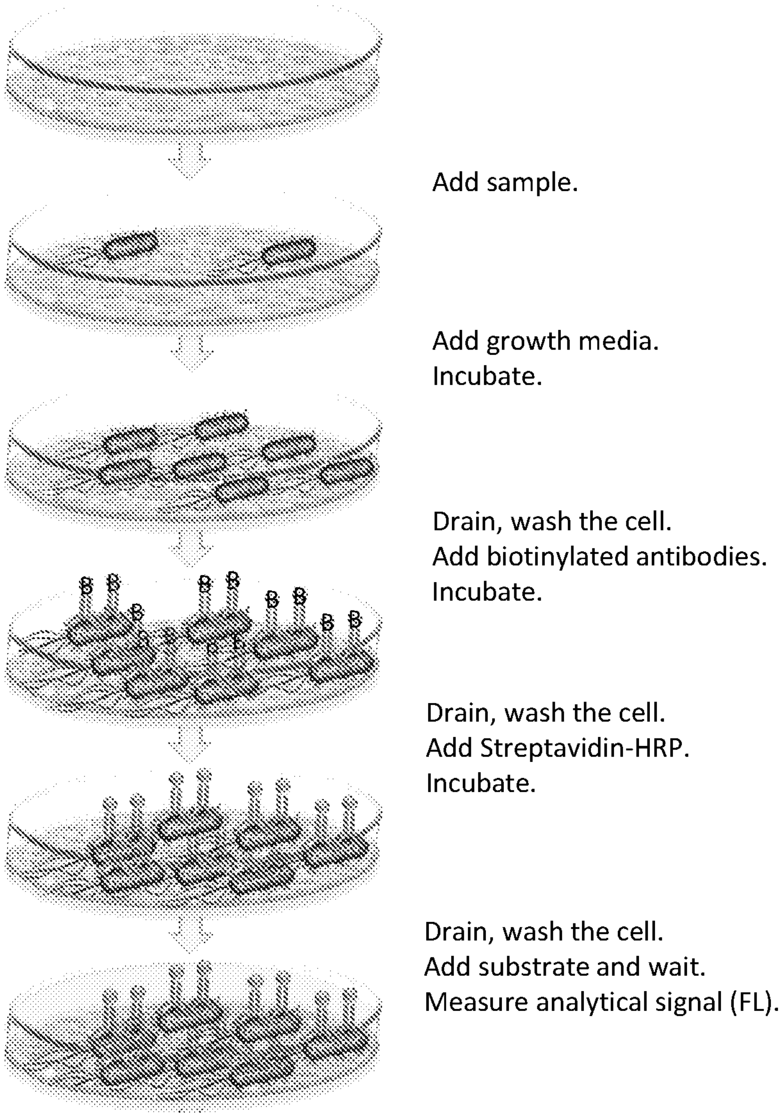
FIG. 15 is an illustration of a second exemplary method comprising the utilization of an ultrasensitive flow-through direct immunoassay ("ultrasensitive FTDI"). In this method, a growth media is used for bacteria proliferation, antibodies are used for bacteria labeling, an enzyme conjugate and a substrate are used for the production of a fluorescent product, and fluorescence is used as the analytical technique for recording the analytical signal.

A representative example is provided for the application of the ultrasensitive FTDI method for the detection of a model case bacteria (*E. coli* ORN 178) in a 10 mL sample and in a 100 mL sample by using a sensor that has multiple flow-permeable sensing compartments (a 96-well filter plates that have a membrane, DuraporePVDF, 0.45 μm pore size, in the bottom of each microwell) and by using fluorescence as the analytical detection technique. Referring to FIG. 15 an exemplary ultrasensitive FTDI method comprises adding/filtering a sample into each microwell so the bacteria present in the sample are trapped on top of the membrane and inside the microwell. The method further comprises culturing the bacteria inside the micro filter well of the well plate by using LB nutrient broth. The method further comprising detecting the bacteria using a biotinylated anti-*E. coli* antibody (as detection antibodies), HRP conjugated with streptavidin (to label the detection antibodies), and Amplex Red and hydrogen peroxide (as an enzymatic substrate). The reaction of HRP with Amplex Red and hydrogen peroxide produces resorufin which can be detected using absorbance, fluorescence, or electrochemical measurements. Fluorescence detection ($\lambda_{ex}$, 540 nm and $\lambda_{em}$, 590 nm) is especially preferred because the fluorescence of the solution of each well can be read inside the well (top-read measurement using a fluorescence plate reader) thereby keeping the risk of sample contamination or user exposure to bacteria low.

An exemplary experiment protocol for this example comprises: adding a sample in a well of the filter well plate previously treated with Superblock™ in PBS; washing the well with 1 mL of PBST 0.05%; adding 300 μL of Mueller-Hinton solution and incubating for 3 hours with mild agitation at 37° C.; draining the well and washing it with 1 mL of PBST 0.05%; adding 100 μL of a 1 μg/mL solution of biotin-labeled *E. coli* antibody and incubating for 1 hour with mild agitation at 37° C.; draining the well and washing it with 2 mL of PBST 0.05%; adding 100 μL of HRP-Streptavidin solution and incubating for 20 minutes with mild agitation at 37° C.; draining the well and washing it with 2 mL of PBST 0.05%; adding 90 μL of the substrate solution comprising Amplex Red and hydrogen peroxide and incubating at 37° C. for 10 min; adding 10 μL of an enzyme stop solution; and reading the fluorescence ($\lambda_{ex}$: 540 nm, $\lambda_{em}$: 590 nm, top reading) within 30 min.

Figure 16A:
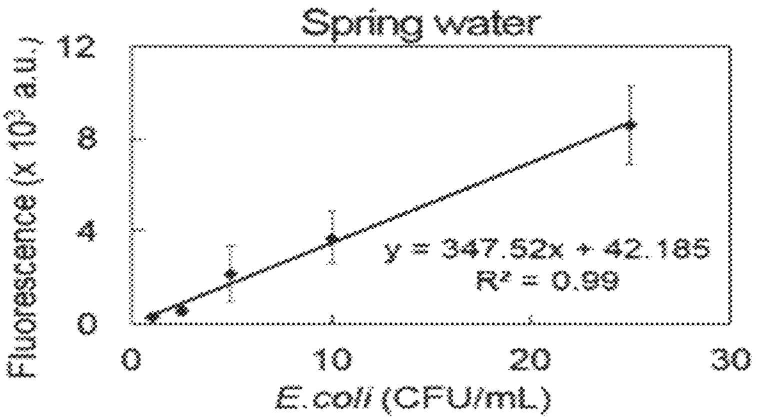
FIG. 16A is an illustration showing a calibration curve of fluorescence intensity of products of a method comprising ultrasensitive FTDI vs the concentration of *E. coli* when 10 mL of natural spring water were analyzed.
Figure 16B:
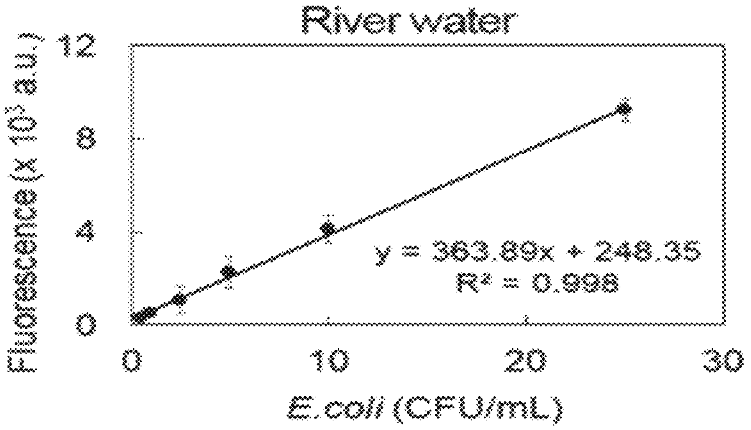
FIG. 16B is an illustration showing a calibration curve of fluorescence intensity of products of ultrasensitive FTDI vs the concentration of *E. coli* when 10 mL of river water were analyzed.
Figure 16C:
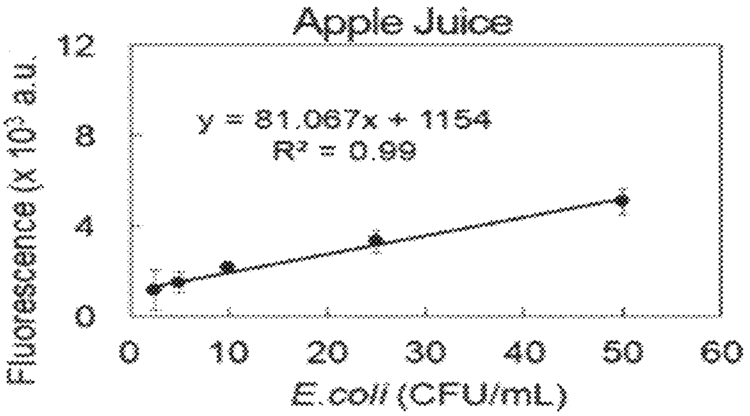
FIG. 16C is an illustration showing a calibration curve of fluorescence intensity of products of ultrasensitive FTDI vs the concentration of *E. coli* when 10 mL of apple juice were analyzed.
Figure 17:
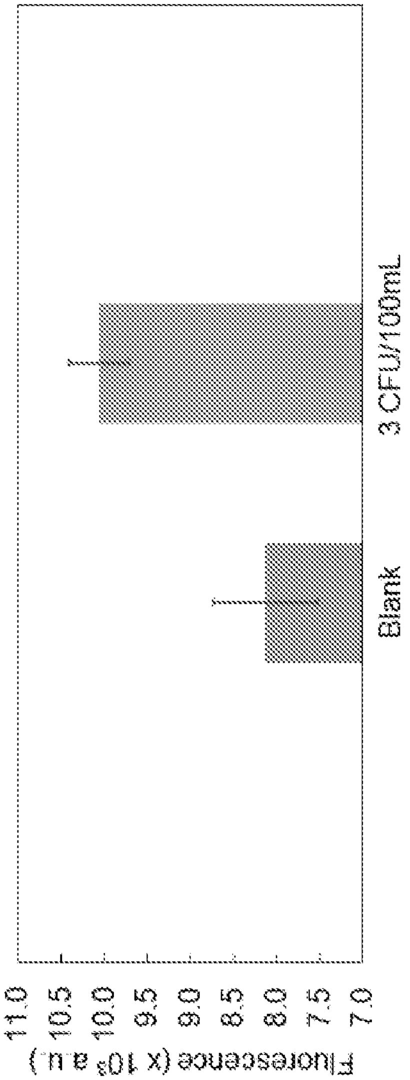
FIG. 17 illustrates a chart illustrating fluorescence signals of blank solutions and positive samples (comprising approx.

To evaluate the performance of the ultrasensitive FTDI method in the analysis of water and juice samples, we prepared calibration curves of the fluorescence signal of the assay mixture (after subtracting the fluorescence of the blank solutions) vs. the concentration of bacteria in bottled water, river water, and apple juices all spiked with *E. coli* bacteria (FIGS. 16A, 16B and 16C). A volume of 10 mL of samples was tested in all cases. It was concluded that the ultrasensitive FTDI method can detect bacteria in levels as low as 2.0, 0.7, and 1.1 CFU/mL. The limit of detection (LOD) was calculated from the standard deviation of the blank solutions ($y_{LOD}=3s_{blank}$). FIG. 17 shows the experimental results when 100 mL of spring water samples were analyzed. An ultrasensitive FTDI assay can detect less than 3 CFU/100 mL and the total analysis time of the assay is 6.5 h when the experimental setup depicted in FIG. 18A was used. A photograph of the experiment set up is shown in FIG. 18B.

The sensitivity of the ultrasensitive FTDI method when analyzing water samples (estimated from the slopes of the calibration curves) was found to be around 40-50 times higher than that found using the rapid FTDI method. Given that the ultrasensitive FTDI uses a 3-hour incubation step, it could be concluded that either there is a significant lag time or the double time during the lag phase of the *E. coli* is around 30 min. Several growth factors (e.g., amino acids, vitamins, antioxidants, etc.) can enhance bacteria growth and reduce double time; therefore, a careful optimization of the conditions of the bacteria proliferation step can lead to even better sensitivity than reported herein.

The intra-assay repeatability of the results of the ultrasensitive FTDI method measured by the average relative standard deviation ("RSD") of triplicates at each concentration level was 5-6%. The relative standard deviation of results of the same samples analyzed on 3 different days ranged from 3 to 8%. Intra-assay repeatability up to 10-15% and inter-assay reproducibility up to 15-20% are satisfactory for immunoassays; therefore, the precision of the method meets acceptable performance standards.

To assess the accuracy of the ultrasensitive FTDI assay, recovery experiments in real river water samples were performed. Filtered river water samples were first spiked with *E. coli* bacteria, and then 10 mL aliquots of the spiked samples were analyzed with the ultrasensitive FTDI assay. The exact number of bacteria in each spiked sample was also determined using the plate agar count assay. The spike recovery was calculated as the % ratio of (*E. coli*$_{added}$-*E. coli*$_{found}$)/*E. coli*$_{added}$. The recoveries of the results of the ultrasensitive FTDI assays are shown in Table 3 (see FIG. 19) and found to range from 80 to 130%. Mean recovery values between 70 and 120% with a relative standard deviation of less than 20% are considered acceptable for the nature of these experiments. The poorer recovery in some samples analyzed with the ultrasensitive FTDI assay can be attributed to higher uncertainty of the true bacteria concentration due to the very low number of bacteria in this samples.

This far, two exemplary methodologies for FTDI assays (one rapid and one ultrasensitive) for the detection of *E. coli* ORN 178 in 10 mL samples using a sensor with multiple flow-permeable sensing compartments have been described. The rapid FTDI assay can be completed in less than 2.5 hours and can detect *E. coli* bacteria in levels down to about 17 CFU/mL. The ultrasensitive FTDI method that was used to analyze the presence of *E. coli* samples can be completed in less than 5.5 hours for 10 mL samples, and 6.5 hours for 100 mL samples, and can detect *E. coli* bacteria in levels lower than about 1 CFU/mL. The performance of the two methodologies was assessed and validated in tap water, river water, and apple juice samples, and the results suggest that the assays are robust, precise, and accurate. The FTDI assays demonstrated herein are direct immunoassays, and, as such, they do not require capture antibodies. Additionally, the total analysis time of rapid FTDI assays is almost half to that of conventional ELISA while the assay is at least 100 times more sensitive.

FTDI assays can analyze sample volumes from a few microliters to many milliliters. The analytical signal in the FTDI assay (contrary to other bacterial assays that can detect bacteria concentration) is related to the number of the bacteria (and not necessarily to the concentration of bacteria in a sample). For example, when various volumes (0.1, 0.5, 3.0, 5.0 and 10 mL) of apple juice samples were spiked with the same number of bacteria (400 *E. coli* bacteria per sample) and analyzed using the rapid FTDI assay, the analytical signal of all the spiked samples was almost constant (see FIG. 20A) while the concentration of the bacteria in each sample was actually different. Given that the analytical signal is related to the total number of bacteria captured in the fluid-permeable sensing compartment, higher volumes of samples should result in higher sensitivity. FIG. 20B shows that even when the same volumes are tested, FTDI assays will provide better results than conventional ELISA assays. FIG. 20C shows that the sensitivity of the rapid FTDI assays is much higher (almost 45 times considering the slope of the calibration curves) when 5 mL of sample are analyzed than 100 μL; and FIG. 20D shows that the detection limit was found 34 times lower for the 5 mL sample compared to the 0.1 mL sample.

Both of the rapid FTDI and the ultrasensitive FTDI methodologies described herein present assays that involve fewer washing steps and are therefore simpler to perform compared to an ELISA, and some of the steps of both the rapid and the ultrasensitive FTDI assays can be easily semiautomated (by using, e.g., a filter plate vacuum manifold and a multichannel peristaltic pump). All the steps of the rapid FTDI and the ultrasensitive FTDI methods (e.g., sample, addition, bacteria proliferation, reagents incubation, washing steps, and signal measurement) may be performed inside of a fluid-permeable sensing compartment, and neither the samples nor the fluid permeable structures need be removed outside of the compartment at any point (until after the final detection step in case of an electrochemical analytical procedure). Consequently, (i) the analytical protocol is relatively easy to perform, (ii) the risk of user exposure to the bacteria is minimal, (iii) the risk of sample contamination is low, (iv) the analytical signal (i.e., fluorescence, absorbance, etc.) can be measured inside the compartment or can be safely pushed out in a separate compartment, and (v) the waste production is low. A possible explanation for the significantly enhanced performance of the rapid and the ultrasensitive FTDI assays compared to conventional ELISA assays for bacteria detection is that all of the bacteria in the sample react in the immunoassay in the case of the rapid and the ultrasensitive FTDI assays while only the bacteria that are captured on the surface of the standard microwell react in the standard ELISA.

FIG. 21 shows a Table 4 that critically compares the rapid FTDI and the ultrasensitive FTDI methods with conventionally known techniques. Table 4 highlights the unique characteristics of these methods compared to conventionally known methods.

For the model case experiment described above, the cost of materials per analyzed sample is less than $1.00 USD (Table 5 in FIG. 22). Therefore, the overall cost of the analysis can be kept relatively low. Since the two methods can be performed in different compartments of an arrays of compartments, the same array can be used for parallel detection of several different bacteria when high affinity, selective antibodies exist for the targeted bacteria. Even when selective antibodies do not exist for some targeted bacteria, the bacteria detection might still be achieved using an approach similar to chemical olfaction because of the great number of tests that can be performed in an array of fluid-permeable sensing compartments.

In another embodiment, an exemplary method for analyzing various volumes of samples ranging from a few microliters to hundreds of milliliters is referred to as the electrochemical flow-through direct immunoassay ("electrochemical FTDI") method. This method can be performed in sensors that are comprised of one or more fluid-permeable sensing compartments. The details about the material of construction, size, and structure of the compartment are described above. In short, the compartment may comprise a syringe filter like device comprising an inlet port and an outlet port. The device preferably houses the fluid-permeable structure which is preferably a membrane, and which is used to capture the bacteria while the sample is passed through the fluid-permeable sensing compartment. The details about the structure and the construction and features of the membrane are described above. In short, the membrane is preferably a porous, fluid-permeable structure having a porosity sufficient to capture the bacteria on the surface while allowing the other part of the metrics to flow through the membrane. The interior of the fluid-permeable sensing compartment may be treated with a reagent to hinder absorption or any type of non-specific binding of bacteria or reagents inside the fluid-permeable sensing compartment. The fluid permeable compartment may comprise two parts, with inlet and outlet ports, with the two parts being attachable by a locking, or a threading system between the two parts. The fluid permeable membrane may be seated in the device. Once the fluid permeable membrane is in place and the two parts are interconnected, the sample may be passed through the inlet and forced out through the outlet. In theory, any volume of sample may be used to pass through the device. After the sample is passed through the fluid-permeable sensing compartment while entrapping the bacteria on the surface of the membrane through any fluid delivery devices, the bottom of the device may be covered to stop the release of subsequently added solutions. In a consequent step, a reagent that may comprise biomolecules such as antibodies raised against the bacteria (anti-bacteria antibodies), nucleic acids/aptamers specific to the bacteria (aptamer sequence that binds to bacteria), antibodies against the bacteria that have been labeled with an enzyme (such as, e.g., HRP, GOx, GDH, Tyr, ALP, β-gal, etc.) or a fluorescent dye (labeled anti-bacteria antibodies), aptamers against the bacteria that are labeled with an enzyme (such as, e.g., HRP, GOx, GDH, Tyr, ALP, β-gal, etc.) or a fluorescence dye (aptamer sequence labeled with an enzyme or a fluorescence dye that binds to bacteria) is added. After adding the solution mentioned above, the top of the compartment may be covered to prevent evaporation of the solution and drying of the fluid-permeable sensing compartment and membrane. After a waiting/incubation time that can be between few seconds to many hours, at a temperature range between 5° C. to 50° C. or above, the solution from the inside of the fluid-permeable sensing compartment is drained and the compartment is washed with a solution that may comprise salts and buffers like phosphate buffer saline, phosphate buffer saline with a surfactant, tris buffer, acetate buffer, etc. If the solution comprises non-labeled antibodies, a solution comprising a reagent such as enzymes (such as, e.g., HRP, GOx, GDH, Tyr, ALP, β-gal, etc.) coupled to proteins (e.g., streptavidin conjugated-HRP, etc.), enzymes (such as, e.g., HRP, GOx, GDH, Tyr, ALP, β-gal, etc.) coupled to antibodies, enzymes (such as, e.g., HRP, GOx, GDH, Tyr, ALP, β-gal, etc.) coupled with aptamers, fluorescent molecules/particles coupled to antibodies, fluorescent molecules/particles coupled to aptamers, is added, after covering the bottom of the cell, followed by a waiting period that may be between few seconds to many hours at the desired temperature, followed by another washing step with buffers. A solution that comprises compounds (such as, e.g., chromogenic or fluorescent or redox active compounds such as TMB, DAB, OPD, ABTS, PNPP, ONPG, Amplex Red, acetaminophen, HQ, etc.) that can participate into enzymatic reactions and oxidizing agents (such as hydrogen peroxide, sodium percarbonate etc.) is added to the fluid-permeable sensing compartment. After a waiting period at the desired temperature, a product that is redox active is produced and its concentration is related to the concentration of bacteria in the tested sample. The reaction product may be determined by using an electroanalytical technique (such as, e.g., amperometry, voltammetry, pulsed voltammetry, square wave voltammetry, etc.) directly inside the fluid-permeable sensing compartment or outside the compartment after drawing some of the reaction product outside of the compartment.

A model case of electrochemical FTDI for a model case bacteria (*E. coli* ORN 178) is described with reference to FIG. 23. The electrochemical FTDI method can determine the concentration of *E. coli* bacteria in 10 mL of spiked water and juice samples but in theory, any volume of sample could be analyzed. The bacteria were detected using biotinylated anti-*E. coli* antibody (as detection antibodies), HRP conjugated with streptavidin (to label the detection antibodies), and Amplex Red and hydrogen peroxide (as an enzymatic substrate). The reaction of HRP with Amplex Red and hydrogen peroxide produces resorufin that can be detected using absorbance, fluorescence, or electrochemical measurements. In the example provided, an electrochemical detection scheme was used. A drop of the solution held inside the fluid-permeable sensing compartment was pushed out of the compartment and placed on top of a screen-printed electrochemical cell, and the current was recoded from the electrochemical reduction of resorufin to dihydroresorufin via a reversible two-electron reduction at around 0.1 V vs. Ag/AgCl of resorufin using square wave voltammetry (pulse sequence: potential range: −0.3 to +0.3 V, frequency: 2 Hz, amplitude: 25 mV, potential step: 5 mV, scan rate: 10 mV/s).

An exemplary method for this model case of electrochemical FTDI comprises: loading a syringe with 10 mL of sample and attached the loaded syringe to the fluid-permeable sensing compartment and adding/passing the sample through the compartment. The same syringe was used to pass some air to drain and air-dry the compartment. The method further comprising: adding 150 μL of 1 μg/mL biotin-labeled anti-*E. coli* antibodies to the compartment, and capping both ports of the compartment with syringe locking caps to perform an incubation step for 60 min at 37° C.; draining the compartment by passing air through the compartment via a syringe; washing the compartment by passing 10 mL of 0.05% PBST using a syringe and then draining and air-drying by passing air through the compartment using the same syringe; adding 120 μL of the HRP conjugated-Streptavidin into the compartment and capping both ports of the compartment with syringe locking caps to perform an incubation step for 25 min at 37° C. under mild shaking; washing the compartment by passing 10 mL of 0.05% PBST and 10 mL PBS through the compartment using a syringe and then draining and air-drying the compartment by passing air using the same syringe; adding 120 μL of substrate solution comprising Amplex Red and hydrogen peroxide to the compartment, capping the outlet port of the compartment, and incubating the compartment for 15 min at room temperature (around 25° C.); adding 10 μL of an enzyme stop solution to the compartment; pushing a drop of the solution held inside the compartment (around 90 μL) out of the compartment and placing the drop on top of a screen-printed electrochemical cell (WE: Carbon, CE: Carbon, RE: Ag) together with 10 μL of 10×PBS; and recording square wave voltammograms using the following pulse sequence: potential range: −0.3-0.3 V, frequency: 2 Hz, amplitude: 25 mV, potential step: 5 mV, scan rate: 10 mV/s. The peak current, around −0.2V, is related to the concentration of bacteria in the tested sample.

The performance of the above-described model electrochemical FTDI assay was evaluated by analyzing 10 mL samples of water and juice spiked with bacteria by preparing calibration curves of the peak current of the square wave voltammograms of the assay mixture (after subtracting the recorded background current of the blank solutions) vs. the concentration of *E. coli* bacteria in spiked deionized water samples, general test water samples, river water samples and apple juice samples (see FIGS. 24-27). The model case electrochemical FTDI achieved limits of detection (LOD) of *E. coli* ORN 178 down to 51 CFU/mL, 130 CFU/mL, 57 CFU/mL, and 80 CFU/mL in deionized water, general test water, real river water, and apple juice samples.

For the model case assay performed using electrochemical FTDI, the intra-assay repeatability of the results of the assays was measured by the average relative standard deviation (RSD) of triplicates at each bacteria concentration level was 5.5%. The average relative standard deviation of results of the same samples analyzed by three different days was 5.6%.

To assess the accuracy of the model case electrochemical FTDI, recovery experiments were performed in real river and pond water samples. The recoveries of the results of the electrochemical FTDI are detailed in Table 6 (see FIG. 28) and were found to range from 71% to 108%. Mean recovery values between 70% and 120% with a relative standard deviation of less than 20% are considered acceptable for the nature of these experiments.

The specificity of the model case electrochemical FTDI assay was examined by testing if the presence of non-target bacteria influences the results of the assays for the determination of the targeted *E. coli* bacteria. One gram-positive strain, *Staphylococcus epidermidis*, and a gram-negative strain *E. coli* BL21 were the non-target bacteria used in the specificity tests. *E. coli* BL21 have no O- or K-antigens in their cell surface and so they will not cross-react with the *E. coli* serotype O/K antibodies used in the assay. FIGS. 29A and 29B show that non-target bacteria do not interfere the assays as the percent recoveries (calculated bacteria concentration with interferences/spiked bacteria concentration) are close to 100%.

Another model case for *E. coli* ORN 178 detection, which is similar to the electrochemical FTDI method described above with reference to FIG. 23 shall now be described with reference to FIG. 30. According to this method, the bacteria are captured inside a fluid-permeable sensing compartment of the sensor and then labeled using biotinylated anti-*E. coli* antibody (as detection antibodies); horseradish peroxidase conjugated with streptavidin (streptavidin HRP) is used to label the detection antibodies; and acetaminophen and sodium percarbonate ($Na_2CO_3 \cdot 1.5H_2O_2$) are used as an enzymatic substrate. The reaction of HRP with acetaminophen and sodium percarbonate produces a reaction mixture that comprises N-acetyl-p-quinoneimine that can be detected using absorbance, or electrochemical measurements. FIG. 31 shows that the absorbance spectrum of this reaction mixture appears maxima at 242 nm (due to the presence of unreacted acetaminophen) and at 320 nm (due to the presence of N-acetyl-p-quinoneimine). N-acetyl-p-quinoneimine is also electrochemical active and can be reduced within the potential window from +0.2 V to −0.2 V vs. Ag/AgCl reference electrode (FIG. 32A) so the presence of N-acetyl-p-quinoneimine inside the reaction mixture can be monitored by using an electrochemical technique such as square wave voltammetry (FIG. 32B). For the results obtained in FIG. 32B, square wave voltammetry was used for the detection of N-acetyl-p-quinoneimine in a drop of the solution held inside the compartment that was pushed out of the compartment and placed on top of a screen-printed electrochemical cell.

A sensor having the shape of syringe holder that comprising a polyvinylidene fluoride (PVDF) membrane was used in this model electrochemical FTDI method. The sensor was pretreated before use by using a solution of 5% bovine serum albumin (BSA) and overnight incubation. The method further comprised: attaching a syringe loaded with 10 mL of sample (or any volume of sample) to the fluid-permeable sensing compartment and adding/passing the sample through the compartment. The same syringe was used to pass some air to drain and air-dry the compartment. The method further comprising: adding 150 μL of the biotinylated antibody solution in phosphate buffer saline 1×(PBS) to the compartment, capping both ports of the compartment with syringe locking caps, and performing an incubation step for 60 min at 25° C.; draining the compartment with an empty syringe by passing air through the compartment a couple of times; washing the compartment by passing 10 mL of PBSTB (1×PBS+0.05% Tween20+0.1% BSA) using a syringe, and then draining and air-drying the compartment by passing air using the same syringe; adding 120 μL of streptavidin-HRP solution in PBS to the compartment, capping both ports of the compartment with syringe locking caps, and performing an incubation step for 25 min at 25° C.; washing the compartment by passing 10 mL of PBSTB and 10 mL PBS through the compartment using a syringe and then draining and air-drying the compartment by passing air through the compartment using the same syringe; adding 120 μL of the substrate solution comprising 0.5 mM acetaminophen and 0.33 mM sodium percarbonate to the compartment and incubating for 10 min at room temperature; pushing a drop of the solution held inside the compartment (around 100 μL) out of the compartment and placing the drop on top of a screen-printed electrochemical cell that has a carbon working electrode; and recording a square wave voltammograms of the reaction mixture using the following parameters: potential range: 0.15 to −0.3 V, frequency: 20 Hz, amplitude: 50 mV, potential step: 5 mV, scan rate: 100 mV/s. The peak current around −0.05 V is related to the concentration of bacteria in the tested sample.

The performance of the above-described model assay in the analysis of 10 mL samples of water was evaluated by preparing calibration curves of the peak current of the square wave voltammograms of the assay mixture (after subtracting the recorded background current of the blank solutions) vs. the concentration of *E. coli* bacteria in spiked water samples (FIG. 33). The model case electrochemical FTDI described with reference to FIG. 30 achieved limits of detection (LOD) of *E. coli* ORN 178 down to 81 CFU/mL.

Another method for analyzing various volumes of samples ranging from a few microliters to hundreds of milliliters includes an ultrasensitive electrochemical flow-through direct immunoassay ("ultrasensitive electrochemical FTDI"). Using this method, samples with very low concentrations of bacteria can be analyzed. Referring to FIG. 34, the ultrasensitive electrochemical FTDI method comprises: passing a collected sample through a fluid-permeable sensing compartment where the bacteria from the sample is captured by the fluid-permeable structure, and the matrix passes through the fluid-permeable structure and is drained from the bottom of the compartment. The draining of the compartment may be facilitated by applying a negative pressure at the outlet port or by applying air at the inlet port. Following that, the outlet port of the sensor may be covered to stop the draining of the solution subsequently added. The method further comprises: adding a growth media to the fluid-permeable sensing compartment to facilitate the proliferation of bacteria. Following the addition of growth media, the inlet of the sensor may be covered to protect the solution from evaporating and the sensing compartment from drying. A waiting/incubation time follows which can be between a few seconds to many hours, at a temperature range between 5° C. to 50° C. or above. Following the waiting/incubation time, the solution from the inside of the fluid-permeable sensing compartment is drained and the compartment is washed with a solution that may comprise salts and buffers like phosphate buffer saline, phosphate buffer saline with a surfactant, tris buffer, acetate buffer etc. In a consequent step, reagent that may comprise biomolecules such as antibodies raised against the bacteria (anti-bacteria antibodies), nucleic acids/aptamers specific to the bacteria (aptamer sequence that binds to bacteria), antibodies against the bacteria that have been labeled with an enzyme (such as HRP, GOx, GDH, Tyr, ALP, β-gal, etc.) or a fluorescent dye (labeled anti-bacteria antibodies), aptamers against the bacteria that are labeled with an enzyme (such as, e.g., HRP, GOx, GDH, Tyr, ALP, β-gal, etc.) or a fluorescence dye (aptamer sequence labeled with an enzyme or a fluorescence dye that binds to bacteria) is added. After a waiting/incubation time that can be between a few seconds to many hours, at the desired temperature, the solution from the inside of the fluid-permeable sensing compartment is drained and the compartment is washed with a solution that may comprise salts and buffers, such as, e.g., a phosphate buffer saline, a phosphate buffer saline with a surfactant, a tris buffer, an acetate buffer, etc. If the solution comprises non-labeled antibodies, a solution comprising a reagent such as enzymes (such as, e.g., HRP, GOx, GDH, Tyr, ALP, β-gal, etc.) coupled to proteins (e.g., streptavidin conjugated-HRP), enzymes (such as HRP, GOx, GDH, Tyr, ALP, β-gal, etc.) coupled to antibodies, enzymes (such as HRP, GOx, GDH, Tyr, ALP, β-gal, etc.) coupled with aptamers, fluorescent molecules/particles coupled to antibodies, fluorescent molecules/particles coupled to aptamers, are added, after covering the bottom of the compartment, followed by a waiting period that may be between few seconds to many hours, followed by another washing step with buffers. Lastly, a solution comprising compounds (e.g., chromogenic or fluorescent or redox active compounds such as TMB, DAB, OPD, ABTS, PNPP, ONPG, Amplex Red, HQ, etc.) that can participate into enzymatic reactions and oxidizing agents (such as hydrogen peroxide, sodium percarbonate etc.) are added to the fluid-permeable sensing compartment. After a waiting period, a product that absorbs into the UV/Vis range, IR range, that emit fluorescence, participate into luminescence reactions, or are redox active is produced and its concentration is related to the concentration of bacteria in the tested sample. The reaction product is determined by using an electrochemical technique (amperometry, voltammetry, pulsed voltammetry, square wave voltammetry) directly inside the fluid-permeable sensing compartment or outside the compartment after drawing some of the reaction product outside the compartment.

The application of the ultrasensitive electrochemical FTDI to a model case for the analysis of a sample comprising *E. coli* ORN 178 shall now be described. Briefly, the electrochemical FTDI described above with reference to FIG. 23 was slightly modified by adding a bacteria enrichment step and a washing step, after the sample was passed through the membrane housed in a fluid-permeable sensing compartment. More specifically, after passing the sample through the fluid-permeable sensing compartment, the cell was filled with growth medium to culture the bacteria captured on the membrane, inside the fluid-permeable sensing compartment. Inlet and outlet ports were sealed using caps and the compartment was incubated for 3 hours at 37° C. The compartment was then drained and washed with buffer, following which, the steps as described above with reference to FIG. 23 were applied.

FIG. 35 demonstrates that the ultrasensitive electrochemical FTDI assay can detect bacteria down to 2.0 CFU/mL in spring water samples. The limit of detection (LOD) was calculated from LOD=3×$S_{intercept}$/slope.

The electrochemical FTDI assays and the ultrasensitive electrochemical FTDI assays referred to in FIGS. 23, 30, and 34 exhibit important advantages over other techniques. For example, unlike conventionally known assays, all of the steps in these methods can occur inside the fluid permeable sensing compartments where the sample and all reagents can be added using disposable syringes to keep the analytical protocol simple and user-friendly. For model assays that demonstrated the detection of *E. coli* in various samples, a robust performance was observed and using the assay, bacteria in concentration levels down to 50 CFU/mL were detected in just 2 hours. The proposed assay, may be optimized further to aid the development of a new generation of portable bacteria biosensors for use in the field because: (a) the methods describe assays that use inexpensive and simple analytical tools (i.e., syringes, syringe filter holder etc.), (b) portable, battery-powered electrochemical analyzers, such as portable fluorometer, etc. can be used to perform analytical measurements in the field or the lab, and transmit the results wirelessly to a cell phone for further analysis and results extraction, and (c) the analytical protocol described in the methods is very simple and does not require sophisticated laboratory skills.

Further disclosed herein is a complete sensing kit for the detection of bacteria in liquid samples by using rapid FTDI, ultrasensitive FTDI, electrochemical FTDI, and ultrasensitive electrochemical FTDI. The kit may comprise few or all of the following: (a) a sensor with one or more fluid-permeable sensing compartments that may be used for the analysis of the liquid samples; (b) all the necessary reagents needed for the assays in liquid or dry form; (c) fluidic tools and attachments (syringes, multipippets, droppers, caps, vacuum systems, pumps, etc.) that may facilitate the addition of samples or reagents in the sensing compartment or in the draining of samples or reagents from the sensing compartments; (d) an incubator; (e) instructions for performing the analytical assay to measure the concentration of bacteria in a sample; (f) a detector for measuring the analytical signals of the assays; and (g) software to correlate the analytical signal to bacteria concentration.

Further disclosed is a complete portable kit for the detection of bacteria in various samples including water samples (bottled water, river water etc.), food samples (fruit juice, beverages milk etc.), and other liquid samples. An exemplary kit comprises a sensor that has a fluid-permeable sensing compartment, and all the necessary reagents and consumables (such as, e.g., fluid delivering devices like a dropper, a pipette, a syringe, etc.) that will allow the assay to detect bacteria, whole bacteria, fragments of bacteria, etc. in liquid samples. The necessary reagent could be in liquid form and/or solid form. Although dry reagents need to be rehydrated before use, they do not need refrigeration and are more stable than liquid reagents when stored, and so, therefore, are preferred over liquid reagents. Nonetheless, in an exemplary embodiment, the kit may comprise both dry and liquid reagents. The complete kit may also include a device to read the analytical signal obtained after performing the analytical protocol for the determination of bacteria, whole bacteria, fragments of bacteria. The device may perform UV/Vis absorbance, fluorescence, or electrochemical measurements. Using the kit, various volumes of samples (ranging from a few microliters to hundreds of milliliters) can be analyzed.

The analytical protocol using a portable kit (Kit B) comprises the following steps. A user would begin by rehydrating the dried reagents by adding them with a predetermined amount of reagent comprising the buffer. If the reagent comprising the buffer is present in the dried form, the user would begin by rehydrating the dried buffer with water. Following the rehydration of all the reagents, the user may pass the sample that needs to be analyzed through the fluid-permeable sensor. The bacteria from the sample would be captured by the fluid-permeable structure, and the matrix would pass through the fluid-permeable structure and would be drained from the bottom of the compartment. The draining of the compartment may be facilitated by applying a negative pressure at the outlet port or by applying air at the inlet port. Following that, the outlet port of the sensor may be covered to stop the draining of the solution that would be added in the next step. In the consequent step, reagent that may comprise biomolecules such as antibodies raised against the bacteria (anti-bacteria antibodies), nucleic acids/aptamers specific to the bacteria (aptamer sequence that binds to bacteria), antibodies against the bacteria that have been labeled with an enzyme (such as, e.g., HRP, GOx, GDH, Tyr, ALP, β-gal, etc.) or a fluorescent dye (labeled anti-bacteria antibodies), aptamers against the bacteria that are labeled with an enzyme (such as, e.g., HRP, GOx, GDH, Tyr, ALP, β-gal, etc.) or a fluorescence dye (aptamer sequence labeled with an enzyme or a fluorescence dye that binds to bacteria) is added, followed by the inlet port being covered to avoid evaporation of the solution, and preventing the fluid-permeable sensor compartment and the fluid-permeable structure from drying. After a waiting/incubation time that can be between a few seconds to many hours, at the desired temperature, the solution from the inside of the fluid-permeable sensing compartment is drained and the compartment is washed with a solution that may comprise salts and buffers like phosphate buffer saline, phosphate buffer saline with a surfactant, tris buffer, acetate buffer, etc. If the solution comprises non-labeled antibodies, a solution comprising among others a reagent such as enzymes (such as, e.g., HRP, GOx, GDH, Tyr, ALP, β-gal, etc.) coupled to proteins (e.g., streptavidin conjugated-HRP), enzymes (such as, e.g., HRP, GOx, GDH, Tyr, ALP, β-gal, etc.) coupled to antibodies, enzymes (such as, e.g., HRP, GOx, GDH, Tyr, ALP, β-gal, etc.) coupled with aptamers, fluorescent molecules/particles coupled to antibodies, fluorescent molecules/particles coupled to aptamers, would be added, after covering the bottom of the cell, followed by a waiting period that may be between few seconds to many hours, followed by another washing step with buffers. Lastly, a solution comprising compounds (chromogenic or fluorescent or redox active compounds such as TMB, DAB, OPD, ABTS, PNPP, ONPG, Amplex Red, acetaminophen, and HQ, etc.) that can participate into enzymatic reactions and oxidizing agents (such as hydrogen peroxide, sodium percarbonate, etc.) are added to the fluid-permeable sensing compartment. After a waiting period a product that absorbs into the UV/Vis range, IR range, that emit fluorescence, participate into luminescence reactions, or is redox active is produced and its concentration is related to the concentration of bacteria in the tested sample. The reaction product may be determined using an analytical technique such as UV/Vis photometry, fluorescence, luminescence, electrochemistry (e.g., amperometry, voltammetry, pulsed voltammetry, square wave voltammetry, etc.), and the like, directly inside the fluid-permeable sensing compartment or outside the compartment after drawing some of the reaction product outside of the compartment. The solution may be pushed out of the outlet using air pressure from the inlet, or the solution may be drawn out using a fluid drawing/delivery device.

The method directly described above herein may be modified to perform an ultrasensitive detection of bacteria in samples. The modification in the procedure includes adding a bacteria growth medium to the fluid-permeable sensing compartment after passing the sample through the device to facilitate the proliferation of bacteria. Following the addition of growth medium, the inlet of the sensor is covered to protect the solution from evaporating and the sensing compartment from drying. Follows is a waiting/incubation time that can be between few seconds to many hours, at a temperature range between 5° C. to 50° C. Following the waiting/incubation time, the solution from the inside of the fluid-permeable sensing compartment may be drained and the compartment may be washed with a solution that may comprise salts and buffers like phosphate buffer saline, phosphate buffer saline with a surfactant, tris buffer, acetate buffer, etc., and the rest of the assay may be carried out in the way described above.

A method for the preparation of room temperature stable pre-stored dried reagents of antibodies and enzymes is also disclosed. Biochemical compounds can be stored in dry form at ambient temperatures inside hydrogels of different polymers and stabilizing agents including trehalose, BSA, polyvinyl alcohol (PVA), Polyvinyl pyrolidone (PVP), gelatin, $FeSO_4$, EDTA, and the like. Experiments demonstrated that biotinylated anti-*E. coli* antibodies and conjugates of streptavidin with horseradish peroxidase (streptavidin-HRP) can be stored sufficiently inside a mixture of Trehalose, BSA, Gelatin, $FeSO_4$, EDTA. A small amount of the mixture (e.g., 20 μL) of the anti-*E. coli* antibody or streptavidin-HRP solutions was added in microcentrifuge tube and dried in a vacuum oven at room temperature overnight. The antibodies and enzyme may be dried in any other container suitable for the application. The dried reagents were stored at room temperature until use up to several days. The pre-stored dried reagents in the hydrogels can be rehydrated when needed with an aqueous solutions buffer consisting of buffers such as phosphate buffer saline, tris buffer, acetate buffer, etc.

A solution of the reagents that needs to be dried, stored, and used later in the assay, may be prepared, and placed in the drying container. The drying of the reagents can be facilitated by vacuum drying at room temperature, which may increase the speed of the process. Once the solution is dried, it may be sealed and stored at room temperature for term use.

Further disclosed is a kit (see FIG. 36) for the detection of *E. coli* ORN 178 bacteria. The kit comprises a sensor (a syringe holder that has a PVDF membrane), 2 plastic droppers, 3 syringes, 2 plastic waste containers, a container with reagent A (dried biotinylated anti-*E. coli* antibodies), a container with reagent B dried (streptavidin-conjugated horseradish peroxidase), a container with reagent C (dried acetaminophen and sodium percarbonate), a 50 mL tube comprising 50 mL PBS, a 50 mL tube comprising PBSTB, a screen printed electrochemical cell that has a carbon working electrode, 4 cap stoppers, and a portable electrochemical analyzer.

The analytical protocol of the kit depicted in FIG. 36 for the detection of model case bacteria (*E. coli* ORN 178) comprises: (#1) The user rehydrate reagent A (dried antibodies) by adding of 200 μL PBS to the micro tube and stirring. (#2) The user rehydrates Reagent B) (dried streptavidin-HRP) by adding 200 μL PBS to the micro tube and stirring. (#3) The user rehydrates Reagent C (acetaminophen and sodium percarbonate mixture) by adding 10 mL of PBS. (#4) The user fills the syringe with the test solution. (#5) The user attaches the syringe to the sensor and adds/passes 10 mL of sample through the sensor. The same syringe is used to pass some air to drain and air-dry the sensing compartment. (#6) The user adds 150 μL of the rehydrated reagent A to the sensor and both ports of the sensor are capped with syringe locking caps to perform an incubation step for 60 min at room temperature. (#7) An empty syringe is used to drain the cell by passing air through it a couple of times. The cell is washed by passing 10 mL of PBSTB using a syringe and then was drained and air-dried by passing air using the same syringe. (#8) 120 μL of the rehydrated reagent B is added into the cell and both ports of the cell are capped with syringe locking caps to perform an incubation step for 25 min at 25° C. (#9) The sensing compartment is drained and washed by passing 10 mL of PBSTB and 10 mL PBS using a syringe and then is drained and air-dried by passing air using the same syringe. (#10) The user adds 120 μL of the rehydrated reagent C in the sensing compartment and incubates it for 10 min at room temperature. (#11) A drop of the solution held inside the cell (around 100 μL) is pushed out of the cell and placed on top of a screen-printed carbon electrode. (#12) Square wave voltammograms of the reaction mixture is recorded using the following parameters: potential range: 0.15 to −0.3 V, frequency: 20 Hz, amplitude: 50 mV, potential step: 5 mV, scan rate: 100 mV/s. The peak current around −0.05 V was related to the concentration of bacteria in the tested sample.

To evaluate the performance of the sensing kit in the analysis of bottled water, river water, apple juice, and skim milk, we prepared calibration curves of the electrochemical current signal of the assay mixture (after subtracting the current of the blank solutions) vs. the concentration of bacteria in bottled water, river water, apple juices and skim milk all spiked with *E. coli* bacteria (FIGS. 37-39). 10 mL samples were analyzed in the cases of bottled water, river water, and apple juice. In case of skim milk, 3 mL skim milk was diluted 10 times with water and analyzed. It was concluded that the kit can detect bacteria in concentrations as low as 14 CFU/mL in bottled water, and 18 CFU/mL in river water, apple juice, and skim milk.

The performance of the kit was tested in the ultrasensitive detection of *E. coli* bacteria in 10 mL and 100 mL of bottled water when two additional steps are added into the analytical protocol described above. The steps were added just after step #5 and include the following: (a) The user fills the sensor that may comprise the *E. coli* ORN 178 pre-concentrated on the membrane of the sensor with 150 μL of LB broth media and incubates the sensor at 37° C. for 3 hours. (b) The sensing compartment is drained and washed by passing 10 mL of PBSTB and 10 mL PBS using a syringe and then is drained and air-dried by passing air using the same syringe. After the completion of these two step the protocol was continued from with step #6. FIG. 41 shows the calibration plots obtained for the detection of *E. coli* spiked in 10 mL of spiked bottled water. FIG. 42 shows the calibration plots obtained for the detection of *E. coli* spiked in 100 mL of spiked bottled water. After the modification, the kit can detect *E. coli* concentrations as low as 1 CFU/mL in 10 mL of sample and 0.1 CFU/mL in 100 mL of sample.

Therefore, it can be seen that the methods and devices disclosed in the present disclosure provide novel improvements to prior art methods and devices for detecting bacteria concentrations in fluid samples, and that they provide dramatically increased sensitivity and accuracy of test analysis at reduced costs per test, and that the methods may be efficiently conducted in the field or at increased sample volume throughput in a lab type environment.

It would be appreciated by those skilled in the art that various changes and modifications can be made to the illustrated embodiments without departing from the spirit of the present invention. All such modifications and changes are intended to be within the scope of the present invention except as limited by the scope of the appended claims.

What is claimed is:

1. A method of detecting bacteria, comprising:

a) obtaining an untreated sample suspected of having bacteria;

b) depositing the sample in a sensor having a fluid-permeable sensing compartment having a fluid-permeable substrate for capturing and retaining bacteria from the sample on or within the substrate;

c) adding a first reagent to the sensor;

d) waiting for a first predetermined time period;

e) removing the first reagent from the sensor;

f) adding a second reagent to the sensor;

g) waiting for a second predetermined time period; and h) via a detector, measuring an analytical signal corresponding to the concentration of bacteria in the sample inside the sensor.

2. The method of claim 1, further comprising the steps of:

adding a third reagent to the sensor;

waiting for a third predetermined time period; and removing the third reagent from the sensor.

3. The method of claim 2, wherein the third reagent is bacteria growth medium and the step of waiting a third predetermined time periods are each, respectively, conducted at a predetermined temperature between about 5° C. to about 50° C.

4. The method of claim 2, further comprising the steps of:

washing the sensor after removing the first reagent from the sensor; and washing the sensor after removing the third reagent from the sensor.

5. The method of claim 2, wherein the sensor further comprises a plurality of sensing compartments.

6. The method of claim 1, wherein the step of waiting a first and second predetermined time periods are each, respectively, conducted at a predetermined temperature between about 5° C. to about 50° C.

7. The method of claim 1, further comprising the steps of:

washing the sensor after removing the first reagent from the sensor.

8. The method of claim 1, further comprising the steps of:

rehydrating the first reagent and the second reagent prior to adding the first reagent and second reagent to the sensor.

9. The method of claim 1, wherein:

the first reagent is selected from the group consisting of antibodies that can bind to whole bacteria or bacterial biomolecules, aptamers/nucleic acids that can bind to whole bacteria or bacteria biomolecules, biotinylated antibodies that can bind to whole bacteria or bacterial biomolecules, enzymes (such as horseradish peroxidase (HRP), glucose oxidase (GOx), glucose dehydrogenase (GDH), tyrosinase (Tyr), alkaline phosphatase (ALP), β-galactosidase (β-gal)) conjugated with proteins (avidin, streptavidin, neutravidin, antibodies) or nucleic acids (DNA, RNA, aptamers); and the second reagent is selected from the group consisting of molecules that are chromogenic or fluorescent or redox active such as 3,3',5,5'-tetramethylbenzidine (TMB), 3,3'-diaminobenzidine (DAB), o-phenylenediamine (OPD), 2,2'-azinobis [3-ethylbenzothiazoline-6-sulfonic acid] (ABTS), p-nitrophenyl phosphate (PNPP), o-nitrophenyl-β-D-galactopyranoside (ONPG), 10-Acetyl-3,7-dihydroxyphenoxazine (Amplex Red), acetaminophen, hydroquinone (HQ), hydrogen peroxide, or sodium percarbonate.

10. The method of claim 9, wherein the first reagent comprises a solution that comprises HRP-labeled anti-bacteria antibody, and the second reagent comprises a solution comprising 10-Acetyl-3,7-dihydroxyphenoxazine (Amplex Red).

11. The method of claim 1, wherein the sensor further comprises a plurality of sensing compartments.

12. A method of detecting bacteria, comprising:

a) obtaining an untreated sample suspected of having bacteria;

b) depositing the sample in a sensor having a fluid-permeable sensing compartment having a fluid-permeable substrate for capturing and retaining bacteria from the sample on or within the substrate;

c) adding a first reagent to the sensor;

d) waiting for a first predetermined time period;

e) removing the first reagent from the sensor;

f) washing the sensor after removing the first reagent from the sensor;

g) adding a second reagent to the sensor;

h) waiting for a second predetermined time period; and i) via a detector, measuring an analytical signal corresponding to the concentration of bacteria in the sample inside the sensor.

13. The method of claim 12, further comprising the steps of:

adding a third reagent to the sensor;

waiting for a third predetermined time period; and removing the third reagent from the sensor.

14. The method of claim 13, wherein the third reagent is bacteria growth medium and the step of waiting a third predetermined time periods are each, respectively, conducted at a predetermined temperature between about 5 °C to about 50 °C.

15. The method of claim 13, further comprising the steps of:

washing the sensor after removing the first reagent from the sensor; and washing the sensor after removing the third reagent from the sensor.

16. The method of claim 12, wherein the step of waiting a first and second predetermined time periods are each, respectively, conducted at a predetermined temperature between about 5 °C to about 50 °C.

17. The method of claim 12, further comprising the steps of:

rehydrating the first reagent and the second reagent prior to adding the first reagent and second reagent to the sensor.

18. The method of claim 12, wherein:

the first reagent is selected from the group consisting of antibodies that can bind to whole bacteria or bacterial biomolecules, aptamers/nucleic acids that can bind to whole bacteria or bacteria biomolecules, biotinylated antibodies that can bind to whole bacteria or bacterial biomolecules, enzymes (such as horseradish peroxidase (HRP), glucose oxidase (GOx), glucose dehydrogenase (GDH), tyrosinase (Tyr), alkaline phosphatase (ALP), ß-galactosidase (ß-gal)) conjugated with proteins (avidin, streptavidin, neutravidin, antibodies) or nucleic acids (DNA, RNA, aptamers); and the second reagent is selected from the group consisting of molecules that are chromogenic or fluorescent or redox active such as 3,3',5,5'-tetramethylbenzidine (TMB), 3,3'- diaminobenzidine (DAB), o-phenylenediamine (OPD), 2,2'-azinobis [3-ethylbenzothiazoline-6-sulfonic acid] (ABTS), p-nitrophenyl phosphate (PNPP), o-nitrophenyl-ß-D-galactopyranoside (ONPG), 10-Acetyl-3,7-dihydroxyphenoxazine (Amplex Red), acetaminophen, hydroquinone (HQ), hydrogen peroxide, or sodium percarbonate.

19. The method of claim 18, wherein the first reagent comprises a solution that comprises HRP-labeled anti-bacteria antibody, and the second reagent comprises a solution comprising 10-Acetyl-3,7-dihydroxyphenoxazine (Amplex Red).

20. The method of claim 12, wherein the sensor further comprises a plurality of sensing compartments.

21. A method of detecting bacteria, comprising:

a) obtaining an untreated sample suspected of having bacteria;

b) depositing the sample in a sensor having a fluid-permeable sensing compartment having a fluid-permeable substrate for capturing and retaining bacteria from the sample on or within the substrate;

c) adding a first reagent to the sensor; the first reagent is selected from the group consisting of antibodies that can bind to whole bacteria or bacterial biomolecules, aptamers/nucleic acids that can bind to whole bacteria or bacteria biomolecules, biotinylated antibodies that can bind to whole bacteria or bacterial biomolecules, enzymes (such as horseradish peroxidase (HRP), glucose oxidase (GOx), glucose dehydrogenase (GDH), tyrosinase (Tyr), alkaline phosphatase (ALP), ß-galactosidase (ß-gal)) conjugated with proteins (avidin, streptavidin, neutravidin, antibodies) or nucleic acids (DNA, RNA, aptamers);

d) waiting for a first predetermined time period;

e) removing the first reagent from the sensor;

f) washing the sensor after removing the first reagent from the sensor;

g) adding a second reagent to the sensor; the second reagent is selected from the group consisting of molecules that are chromogenic or fluorescent or redox active such as 3,3',5,5'-tetramethylbenzidine (TMB), 3,3'-diaminobenzidine (DAB), o-phenylenediamine (OPD), 2,2'-azinobis [3-ethylbenzothiazoline-6-sulfonic acid] (ABTS), p-nitrophenyl phosphate (PNPP), o-nitrophenyl-ß-D-galactopyranoside (ONPG), 10-Acetyl-3,7-dihydroxyphenoxazine (Amplex Red), acetaminophen, hydroquinone (HQ), hydrogen peroxide, or sodium percarbonate;

h) rehydrating the first reagent and the second reagent prior to adding the first reagent and second reagent to the sensor;

i) waiting for a second predetermined time period; and j) via a detector, measuring an analytical signal corresponding to the concentration of bacteria in the sample inside the sensor.

* * * * *